(12) United States Patent
White et al.

(10) Patent No.: US 6,825,176 B2
(45) Date of Patent: Nov. 30, 2004

(54) E2 DISPLACEMENT ASSAY FOR IDENTIFYING INHIBITORS OF HPV

(75) Inventors: Peter White, Montreal (CA); Christiane Yoakim, Laval (CA)

(73) Assignee: Boehringer Ingelheim (Canada) Ltd., Laval (CA)

( * ) Notice: Subject to any disclaimer, the term of this patent is extended or adjusted under 35 U.S.C. 154(b) by 0 days.

(21) Appl. No.: 10/358,790

(22) Filed: Feb. 5, 2003

(65) Prior Publication Data

US 2003/0194698 A1 Oct. 16, 2003

Related U.S. Application Data

(60) Provisional application No. 60/355,711, filed on Feb. 7, 2002.

(51) Int. Cl.[7] .................. A01N 43/04; A01N 61/00; A01N 37/18; A01N 31/44; A61K 31/535
(52) U.S. Cl. .................. 514/44; 435/6; 514/1; 514/152; 514/231.5; 514/351; 536/23.1; 548/127
(58) Field of Search .................. 435/6; 514/1, 44, 514/351, 152, 231.5; 536/23.1; 548/127

(56) References Cited

FOREIGN PATENT DOCUMENTS

WO     WO-0250082 A2    6/2002

OTHER PUBLICATIONS

Stratagene 1988 catalog p. 39.*

* cited by examiner

Primary Examiner—Jezia Riley

(74) Attorney, Agent, or Firm—Raymond P. Raymond; Michael Morris; David A. Dow

(57) ABSTRACT

The present invention generally relates to an assay for identifying inhibitors of Human Papillomavirus (HPV), comprising:

a) contacting a HPV E2 transactivation domain with a probe to form a E2:probe complex and measuring a signal from said probe to establish a base line level;

b) incubating the E2:probe complex with a test compound and measuring the signal from said probe;

c) comparing the signal from step b) with the signal from step a);

wherein said probe is a compound of formula (I) or its enantiomers or diastereoisomers thereof:

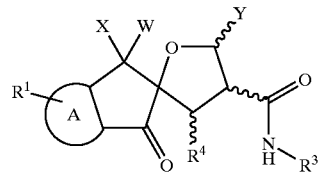

(I)

wherein $R^1$, A, X, W, Y, $R^3$ and $R^4$ are as defined herein; or a derivative thereof, wherein said derivative is a probe of formula (I) labeled with a detectable label or an affinity tag, wherein wavy lines represent bonds of unspecified stereochemistry; and wherein said signal is selected from: fluorescence, resonance energy transfer, time resolved fluorescence, radioactivity, fluorescence polarization, change in the intrinsic spectral properties, luminescence and plasma-resonance; whereby a modulation in said signal is an indication that said test compound binds to said transactivation domain.

31 Claims, 6 Drawing Sheets

E2 DISPLACEMENT ASSAY FOR IDENTIFYING INHIBITORS OF HPV

RELATED APPLICATIONS

Benefit of U.S. Provisional Application, Ser. No. 60/355,711, filed on Feb. 7, 2002, is hereby claimed.

FIELD OF THE INVENTION

The present invention generally relates to an assay for identifying inhibitors of the papilloma virus (PV), particularly human papilloma virus (HPV). In particular, the present invention provides a novel probe in a competitive assay to identify HPV inhibitors. More particularly, the present invention relates to the synthesis and use of a probe that binds with specificity to the transactivation domain (TAD) of HPV E2 to form a complex therewith, and which is capable of being displaced by inhibitors of HPV.

BACKGROUND OF THE INVENTION

Papillomaviruses are non-enveloped DNA viruses that induce hyperproliferative lesions of the epithelia. The papillomaviruses are widespread in nature and have been identified in higher vertebrates. Viruses have been characterized, amongst others, from humans, cattle, rabbits, horses, and dogs. The first papillomavirus was described in 1933 as cottontail rabbit papillomavirus (CRPV). Since then, the cottontail rabbit as well as bovine papillomavirus type 1 (BPV-1) have served as experimental prototypes for studies on papillomaviruses. Most animal papillomaviruses are associated with purely epithelial proliferative lesions, and most lesions in animals are cutaneous. In the human there are more than 75 types of papillomavirus that have been identified and they have been catalogued by site of infection: cutaneous epithelium and mucosal epithelium (oral and genital mucosa). The cutaneous-related diseases include flat warts, plantar warts, etc. The mucosal-related diseases include laryngeal papillomas and anogenital diseases such as cervical carcinomas.

There are more than 25 HPV types that are implicated in anogenital diseases, these are grouped into "low risk" and "high risk" types. The low risk types include HPV type 6 and type 11 and induce mostly benign lesions such as condyloma acuminata (genital warts) and low grade squamous intraepithelial lesions (SIL). In the United States, 1% of the sexually active population has genital warts of which 90% is attributed to HPV-6 and HPV-11.

The high risk types are associated with high grade SIL and cervical cancer and include most frequently HPV types 16, 18, 31, 33, 35, 45, 52, and 58. The progression from low-grade SIL to high-grade SIL is much more frequent for lesions that contain high risk HPV-16 and 18 as compared to those that contain low risk HPV types. In addition, only four HPV types are detected frequently in cervical cancer (types 16, 18, 31 and 45). About 500,000 new cases of invasive cancer of the cervix are diagnosed annually worldwide.

The life cycle of PV is closely coupled to keratinocyte differentiation. Infection is believed to occur at a site of tissue disruption in the basal epithelium. Unlike normal cells, the cellular DNA replication machinery is maintained as the cell undergoes vertical differentiation. As the infected cells undergo progressive differentiation the viral genome copy number and viral gene expression in turn increase, with the eventual late gene expression and virion assembly in terminally differentiated keratinocytes and the release of viral particles.

The coding strands for each of the papillomavirus contain approximately ten designated translational open reading frames (ORFs) that have been classified as either early ORFs or late ORFs based on their location in the genome. E1 to E8 are expressed early in the viral replication cycle, and two late genes (L1 and L2) encode the major and minor capsid proteins respectively. The E1 and E2 gene products function in viral DNA replication, whereas E5, E6 and E7 are expressed in connection with host cell proliferation. The L1 and L2 gene products are involved in virion structure. The function of the E3 and E8 gene products is uncertain at present.

Studies of HPV have shown that proteins E1 and E2 are the only two viral proteins that are necessary for viral DNA replication in vitro and in vivo, in addition to the host DNA replication machinery. This requirement is similar to that of bovine papillomavirus type 1 (BPV-1). Indeed, there is a high degree of similarity between E1 and E2 proteins and the ori-sequences of all papillomaviruses (PV) regardless of the viral species and type. Evidence emanating from studies of BPV-1 have shown that E1 possesses ATPase and helicase activities that are required in viral DNA replication.

The E2 protein is a transcriptional activator that binds to E1 protein and forms a complex that binds specifically to the ori sequence (Mohr et al., 1990, Science 250:1694–1699). It is believed that E2 enhances binding of E1 to the BPV origin of replication (Seo et al., 1993, Proc. Natl. Acad. Sci., 90:2865–2869). In HPV, Lui et al. suggested that E2 stabilizes E1 binding to the ori (1995, J. Biol. Chem., 270(45): 27283–27291). The HPV-16 transactivation domain (TAD) of E2 has been described in J. E. Burns et al., 1998 (Acta Cryst. D54, 1471–1474) and amino acids 1–190 were found to be required and sufficient for E1 binding (Yasugi et al., 1997, J. Virol. 71, 891–899).

To thwart this disease, a chemical entity that would interfere with or inhibit viral DNA replication is therefore desirable. Previously described methods to evaluate inhibitors of the E1–E2 interaction (U.S. Pat. No. 5,925,516 and Titolo et al. 1999, J. Virol. 73, 5282–5293) have relied on the production of full-length E1 and E2 proteins. HPV E2 and especially E1 have been difficult to obtain in sufficient quantity and purity for effective drug screening (White et al., 2001, J. Biol. Chem., 276(25), 22426–22438; Rocque et al., 2000, Protein, Expression Purif. 18, 148–159). Furthermore, one common assay for this interaction involves measuring the cooperative binding of E1 and E2 to double-stranded DNA referred to herein as the E2-dependent E1 DNA binding assay (Titolo et al. 1999, J. Virol. 73, 5282–5293). This method is highly sensitive to salt concentration and pH, as is well known to be true in general for protein-DNA interactions. Furthermore, protein-DNA interactions are sensitive to inhibition by nonspecific DNA intercalators (Lai et al., 1992, Proc Natl. Acad. Sci. USA, 89(15):6958–62).

One family of chemical entities that inhibit HPV replication is disclosed in WO 02/50082 published Jun. 27, 2002. The mechanism of action of these inhibitors was elucidated and they were found to inhibit the E1–E2 interaction by binding to the E2 TAD. We have therefore rationalized that, used as probes, these could be displaced by test compounds that also inhibit or disrupt the E1:E2 interaction, an interaction that is critical for the complex to bind to DNA and proceed with viral replication. Validation of this rationale could be obtained by testing the inhibitors identified in the present assay with a well known E2-dependent E1-DNA binding assay.

The present invention therefore provides a probe and a novel displacement assay for screening for potential inhibitors of papilloma viral replication. Advantageously, this displacement assay of the present invention is easy to use and inexpensive and amenable to adjustments in salt concentration or pH levels. This type of assay is also amenable to a high sensitivity and a high throughput format, and uses a protein that has a low molecular weight, which is easy to purify.

It is a further advantage of the present invention to provide a probe that binds to the transactivation domain of HPV E2 with a high affinity, and which is displaced by inhibitors of HPV.

The present description refers to a number of documents, the content of which is herein incorporated by reference.

SUMMARY OF THE INVENTION

In a first embodiment, the invention provides a probe of formula (I) or its enantiomers or diastereoisomers thereof:

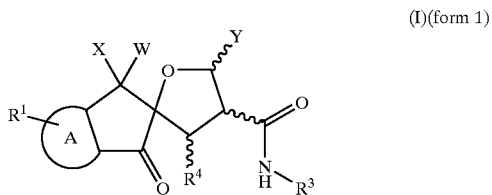

(I)(form 1)

wherein:

A is a 5- or 6-membered homocyclic ring, or a 5- or 6-membered heterocyclic ring containing 1 or more heteroatoms selected from N, O and S;

X is H and W is OH; or X and W together form a carbonyl group or an epoxide;

$R^1$ is H; or one or two substituents independently selected from the group consisting of: hydroxy, halo, lower alkyl, lower alkoxy, lower thioalkyl, haloalkyl (e.g. trifluoromethyl), or —C(O)$R^2$ wherein $R^2$ is lower alkyl, aryloxy or benzyloxy;

Y is phenyl optionally mono- or di-substituted with $R^5$ or C(O)$R^6$, wherein $R^5$ is lower alkyl, lower cycloalkyl, lower alkoxy, halo, hydroxy, nitrile or trifluoromethyl, and $R^6$ is lower alkyl, lower cycloalkyl, lower alkoxy, hydroxy or trifluoromethyl; said phenyl ring being optionally fused with a saturated or unsaturated 4 to 6-membered ring optionally containing a heteroatom selected from N, O and S;

or Y is a heterocycle (Het) containing one or more heteroatom selected from N, O or S, said Het optionally mono- or di-substituted with $R^5$ or C(O)$R^6$, wherein $R^5$ and $R^6$ are as defined above; said Het being optionally fused with a saturated or unsaturated 4 to 6-membered ring optionally containing a heteroatom selected from N, O and S;

or Y is ethylene-phenyl, said ethylene moiety being optionally mono-substituted with lower alkyl, wherein said phenyl ring is optionally mono- or di-substituted with $R^5$ or C(O)$R^6$, wherein $R^5$ and $R^6$ are as defined above; said phenyl ring being optionally fused with a saturated or unsaturated 4- to 6-membered ring optionally containing a heteroatom selected from N, O and S;

or Y is ethylene-Het, said ethylene moiety being optionally mono-substituted with lower alkyl, wherein Het is optionally mono- or di-substituted with $R^5$ or C(O)$R^6$, wherein $R^5$ and Re are as defined above; said Het being optionally fused with a saturated or unsaturated 4 to 6-membered ring optionally containing a heteroatom selected from N, O and S;

$R^3$ is selected from the group consisting of: lower alkyl, lower cycloalkyl, lower alkylene, aryl or lower aralkyl, all of which optionally mono- or di-substituted with:

lower alkyl, lower cycloalkyl, haloalkyl, halo, CN, azido, lower alkoxy, (lower alkyl)acyl, $C_{1-6}$ thioalkyl, $C_{1-6}$ alkylsulfonyl, NHC(O)-lower alkyl, NHC(O)-aryl, NHC(O)—O-lower alkyl, NHC(O)O-aryl, aryl, aryloxy, hydroxy, nitro, amino, or Het, said Het optionally mono- or di-substituted with lower alkyl, lower cycloalkyl, lower alkoxy, halo, hydroxy, nitrile, trifluoromethyl, C(O)$R^6$ wherein $R^6$ is as defined above;

said lower cycloalkyl, aryl, lower aralkyl or Het being optionally fused with a saturated or unsaturated 4 to 6-membered ring optionally containing a heteroatom selected from N, O and S; and $R^4$ is a carboxylic acid, a salt or an ester thereof;

or a derivative thereof;

wherein said derivative is a probe of Formula (I) labeled with a detectable label or an affinity tag, wherein wavy lines represent bonds of unspecified stereochemistry; and wherein said probe binds to the transactivation domain of HPV E2 and is capable of being displaced by a potential inhibitor thereof: or a derivative thereof, wherein said derivative is a probe of formula (I) labeled with a detectable label or an affinity tag, wherein wavy lines represent bonds of unspecified stereochemistry; and wherein said signal is selected from: fluorescence, resonance energy transfer, time resolved fluorescence, radioactivity, fluorescence polarization, change in the intrinsic spectral properties, luminescence and plasma-resonance; whereby a modulation in said signal is an indication that said test compound binds to said transactivation domain.

Alternatively, the first embodiment of the invention provides compounds having the following formulae, selected from the group consisting of:

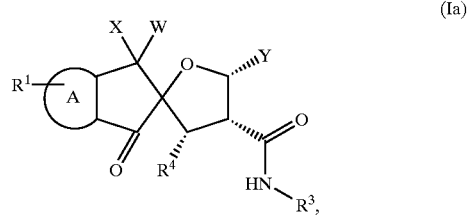

(Ia)

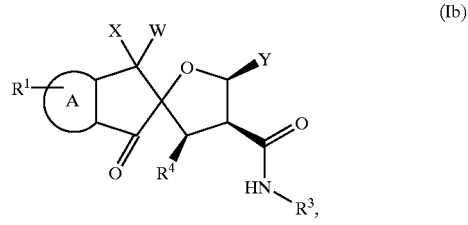

(Ib)

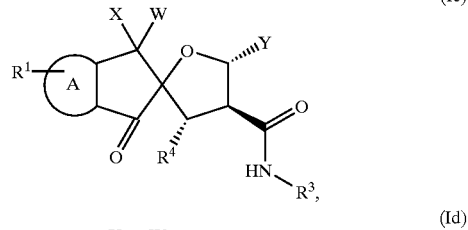

(Ic)

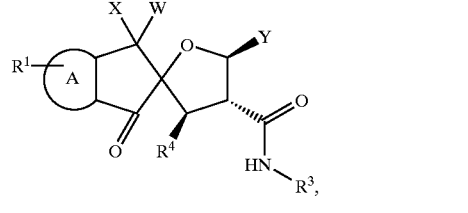

(Id)

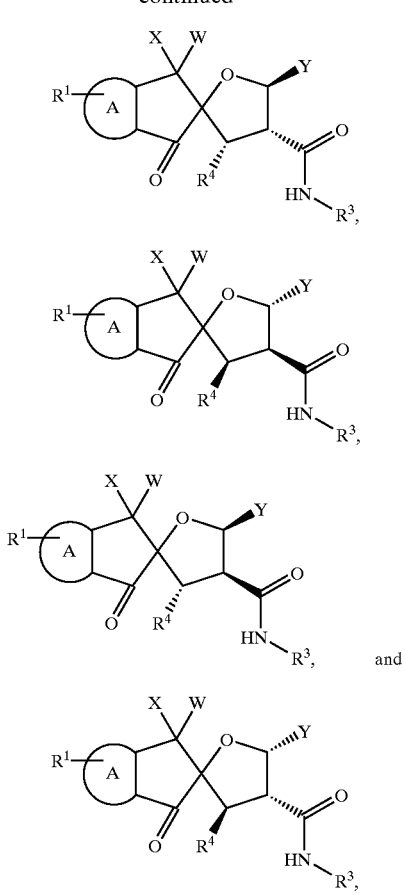

wherein $R^1$, A, X, W, Y, $R^3$ and $R^4$ are as defined above.

Compounds of formula I may also be represented by forms (2) and (3):

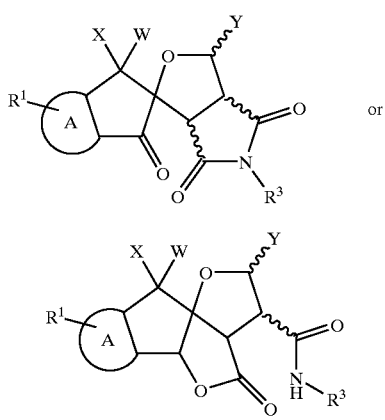

wherein $R^1$, A, X, W, Y and $R^3$ are as defined above.

As will be recognized by persons skilled in the art, the compounds in forms (2) and (3) are readily converted to compounds of formula (I) in form (1). Without wishing to be bound by theory, it is believed that the compounds of formula (I) are in equilibrium between forms (1), (2) or (3) depending on the solvent and the pH in which they are dissolved. It has however been demonstrated that compounds of formula (I) are biologically active in form (1), and that the compounds in forms (2) and (3) will hydrolyze in conditions reproducing mammalian plasma (pH 7.4) to yield biologically active form (1).

According to a second embodiment of the invention, there is provided an assay for the identification of inhibitors of HPV replication, comprising:
 a) contacting a transactivation domain of HPV E2 protein with a probe of formula I as defined above to form an E2:probe complex and measuring a signal from said probe to establish a base line level;
 b) incubating a E2:probe complex with a test compound and measuring the signal from said probe in said complex; and
 c) comparing the signal from step a) with the signal from step b);
whereby a modulation in said signal is an indication that said test compound binds to said transactivation domain.

As will be understood by a person skilled in the art, steps a) and b) in the above mentioned assay may be carried out in sequence or in parallel i.e. the control signal from the E2:probe can be measured prior to the addition of the test compound or the control signal can be measured in a well distinct from the well where the E2:probe complex is mixed with the test compound.

An alternative aspect of this second embodiment provides an assay for the identification of inhibitors of HPV replication, comprising:
 a) contacting a transactivation domain of HPV E2 protein with a probe of formula I as defined above to form an E2:probe complex and measuring a signal from said probe to establish a base line level;
 b) incubating a E2 protein with a test compound;
 b') adding a probe of formula (I) to said mixture of E2 and test compound from step b) and measuring the signal from said probe; and
 c) comparing the signal from step a) with the signal from step b');
whereby a modulation in said signal is an indication that said test compound binds to said transactivation domain.

As will be understood by a person skilled in the art, steps a) and b) in the above mentioned assays are usually carried out in parallel i.e. the control signal from the E2:probe is measured in a well distinct from the well where the E2:test compound is mixed with the probe.

As will be understood by a person skilled in the art, the probe of formula (I) used for the present assay can be replaced without undue burden by any alternative compound found in WO 02/50082 incorporated herein by reference.

As will be understood by a person skilled in the art, modulation in the signal means either a decrease or an increase in the signal. Usually, modulation in the signal will be observed as a decrease in signal.

According to a third embodiment of the invention, there is provided the use of a probe according to formula (I) in the development of an assay for identifying inhibitors of HPV replication.

According to a fourth embodiment of the invention, there is provided a kit for testing compounds that potentially bind to the transactivation domain of HPV, said kit comprising a probe according to formula (I); and instructions on how to use said probe for identifying test compounds binding to said transactivation domain.

According to a fifth embodiment of the invention, there is provided a reagent for testing compounds that potentially bind to the transactivation domain of HPV E2, said reagent comprising a E2:probe complex as defined above.

BRIEF DESCRIPTION OF THE DRAWINGS

Having thus generally described the invention, reference will now be made to the accompanying drawings, showing by way of illustration preferred embodiments thereof, and in which.

DETAILED DESCRIPTION OF PREFERRED EMBODIMENTS

Definitions

Figure 1:
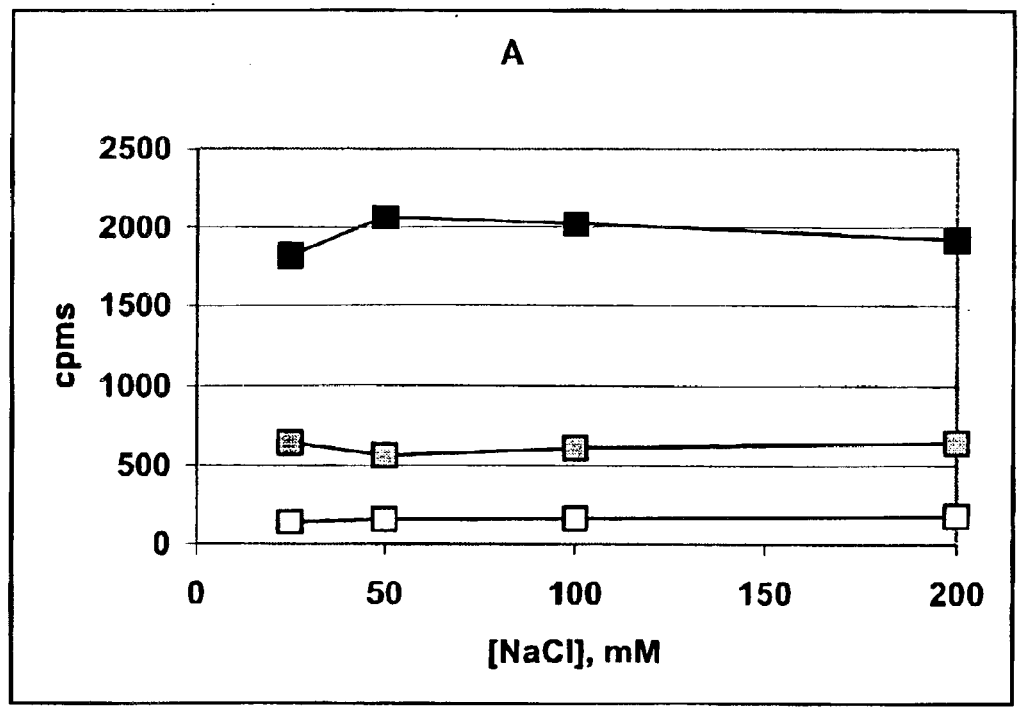
FIG. 1 shows a graph of a ligand displacement assay showing the effect of different concentrations of NaCl (A) or KCl (B) on the assay. For each salt, radioactivity is given for wells with TAD and probe (black), probe only, without TAD (white), and TAD, probe, and a standard inhibitor (gray)
Figure 1:
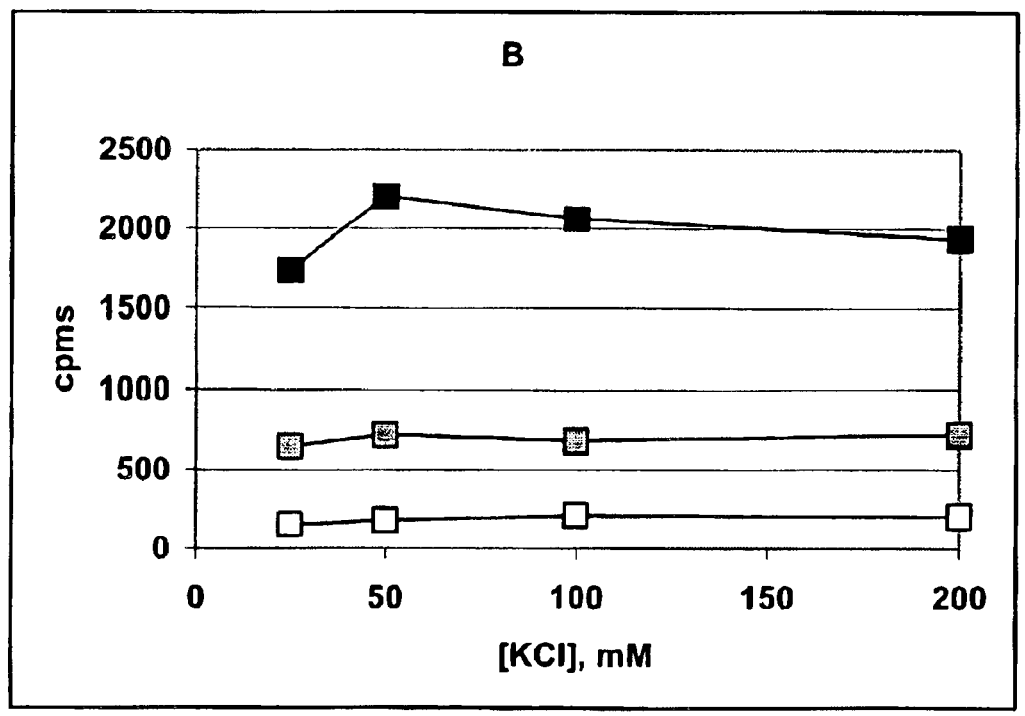

As used herein, the following definitions apply unless otherwise noted:

As used herein, the term "derivative" is intended to mean "detectable label" or "affinity tag". The term "detectable label" refers to any group that may be linked to the transactivation domain of HPV E2 or to a probe of the present invention such that when the probe is associated with the domain, such label allows recognition either directly or indirectly of the probe such that it can be detected, measured and quantified. Examples of such "labels" are intended to include, but are not limited to, fluorescent labels (such as fluorescein, Oregon green, dansyl, rhodamine, tetra-methyl rhodamine, Texas-red, phycoerythrin BODIPYO® FL, BODIPY® 493/503 or $Eu^{3+}$), chemiluminescent labels (such as luciferase), calorimetric labels, enzymatic markers, radioactive isotopes (such as $^{3}H$, $^{14}C$, $^{125}I$) and affinity tags such as biotin. Such labels can be attached to the probe or to the transactivation domain of HPV E2 by well known methods.

The term "affinity tag", as used herein, refers to a ligand (that is linked to the transactivation domain of HPV E2 or to a probe of the present invention) whose strong affinity for a receptor can be used to extract from a solution the entity to which the ligand is attached. Examples of such ligands include biotin or a derivative thereof, a poly-histidine peptide, an amylose sugar moiety or a defined epitope recognizable by a specific antibody. Such affinity tags are attached to the probe or to the transactivation domain of HPV E2 by well known methods.

As used herein the term "probe" refers to a compound of formula (I) that is capable of binding to the transactivation domain of HPV E2 in a covalent or non-covalent manner. When the probe is bound in a non-covalent manner, it can be displaced by a test compound. When bound in a covalent manner, the probe can be used for cross-linking experiments wherein the HPV E2 adduct formation can be quantified and inhibited by test compounds.

The term "halo" as used herein means a halogen radical selected from bromo, chloro, fluoro or iodo.

The term "lower alkyl" (or $C_{1-6}$ alkyl) as used herein, either alone or in combination with another radical, means straight or branched-chain alkyl radicals containing up to six carbon atoms and includes methyl, ethyl, propyl, butyl, hexyl, 1-methylethyl, 1-methylpropyl, 2-methylpropyl and 1,1-dimethylethyl. The term "$C_{0-6}$ alkyl" preceding a radical means that this radical can optionally be linked through a $C_{1-6}$ alkyl radical or the alkyl may be absent ($C_0$).

The term "lower cycloalkyl" as used herein, either alone or in combination with another radical, means saturated cyclic hydrocarbon radicals containing from three to seven carbon atoms and includes cyclopropyl, cyclobutyl, cyclopentyl, cyclohexyl and cycloheptyl.

The term "lower alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as tert-butoxy.

The term "haloalkyl" as used herein means alkyl radical containing one to six carbon atoms wherein one or more hydrogen atom is replaced by a halogen atom (e.g. trifluoromethyl).

The term "amino" as used herein means an amino radical of formula —$NH_2$. The term "lower alkylamino" as used herein means alkylamino radicals containing one to six carbon atoms and includes methylamino, propylamino, (1-methylethyl)amino and (2-methylbutyl)amino. The term "di(lower alkyl)amino" means an amino radical having two lower alkyl substituents each of which contains one to six carbon atoms and includes dimethylamino, diethylamino, ethylmethylamino and the like.

The term "acyl" as used herein, either alone or in combination with another radical, refers to groups —C(O)R.

The term "aryl" as used herein, either alone or in combination with another radical, means either an aromatic monocyclic system containing 6 carbon atoms or an aromatic cyclic system containing 10 carbon atoms. For example, aryl includes phenyl or naphthalene.

The term "$C_{7-16}$ aralkyl" as used herein, either alone or in combination with another radical, means an aryl as defined above linked through an alkyl group, wherein alkyl is as defined above containing from 1 to 6 carbon atoms. Aralkyl includes for example benzyl, and butylphenyl.

The term "homocyclic ring" as used herein means a monovalent radical derived by removal of a hydrogen from a five- or six-membered, saturated or unsaturated non-heterocyclic ring. One preferred type of homocycle is a carbocycle made up of carbon atoms (including aryls).

The term "Het" or "heterocycle" as used herein means a monovalent radical derived by removal of a hydrogen from a five- or six-membered, saturated or unsaturated ring containing from one to three heteroatoms selected from nitrogen, oxygen and sulfur. Optionally, the heterocycle may bear one or two substituents; for example, N-oxido, lower alkyl, ($C_{1-3}$)alkyl-phenyl, lower alkoxy, halo, amino or lower alkylamino. Again optionally, the five- or six-membered heterocycle can be fused to a second cycloalkyl, an aryl (e.g. phenyl) or another heterocycle.

Examples of suitable heterocycles and optionally substituted heterocycles include morpholine, thiadiazole, quinoline, 3,4-methylene-dioxyphenyl, benzothiazole, pyrrolidine, tetrahydrofuran, thiazolidine, pyrrole, 1H-imidazole, 1-methyl-1H-imidazole, pyrazole, furan, thiophene, oxazole, isoxazole, thiazole, 2-methylthiazole, 2-aminothiazole, 2-(methylamino)-thiazole, piperidine, 1-methylpiperidine, 1-methylpiperazine, 1,4-dioxane, pyridine, pyridine N-oxide, pyrimidine, 2,4-dihydroxypyrimidine, 2,4-dimethylpyrimidine, 2,6-dimethylpyridine, 1-methyl-1H-tetrazole, 2-methyl-2H-tetrazole, benzoxazole and thiazolo[4,5-b]-pyridine.

With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group.

In particular the esters may be a $C_{1-16}$ alkyl ester, an unsubstituted benzyl ester or a benzyl ester substituted with at least one halogen, $C_{1-6}$ alkyl, $C_{1-6}$ alkoxy, nitro or trifluoromethyl.

Preferred Embodiments

Probe

The probes of the present invention can be synthesized as racemic mixtures and then can be separated in their respective single diastereoisomers. All such diastereoisomers and mixtures are contemplated within the scope of the present invention.

Preferably, such diastereoisomers include mixture of compounds with the following relative stereochemistry between [Y & C(O)NH—R³] and [C(O)NH—R³ & R⁴] where formulas (Ia) and (Ib) both represent racemic mixtures of compounds with the relative stereochemistry referred to as "cis/cis":

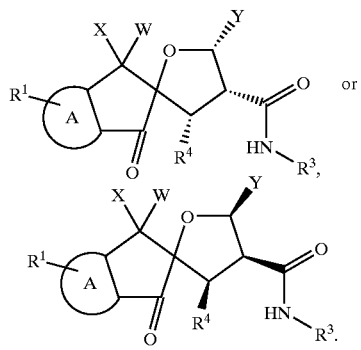

(Ia)

(Ib)

Formulas (Ic) and (Id) both represent racemic mixtures of compounds with the relative stereochemistry referred to as "trans/trans":

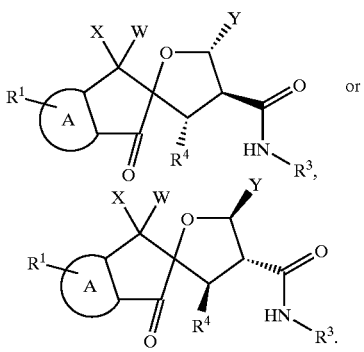

(Ic)

(Id)

Formulas (Ie) and (If) both represent racemic mixtures of compounds with the relative stereochemistry referred to as "trans/cis":

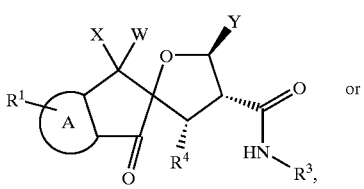

(Ie)

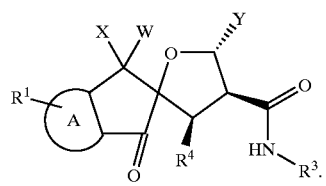

(If)

Formula (Ig) and (Ih) both represent racemic mixtures of compounds with the relative stereochemistry referred to as "cis/trans":

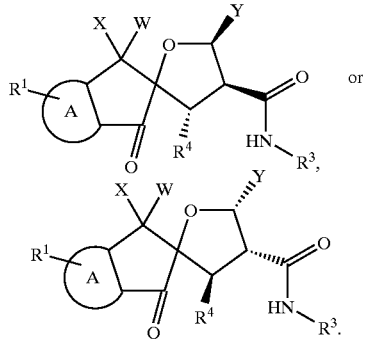

(Ig)

(Ih)

More preferably, compounds of formula (I), present in an "cis/cis" relative stereochemistry can also be represented as follows:

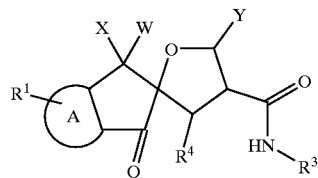

racemic mixture of Ia and Ib

Most preferably, the invention comprises pure enantiomers of compounds of formula (Ia) or (Ib) with the relative stereochemistry "cis/cis":

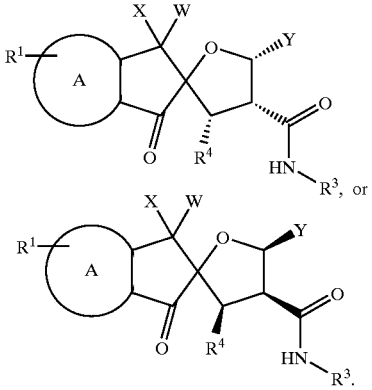

(Ia)

(Ib)

With respect to all of the above-mentioned compounds, A is preferably a phenyl ring or a 5-membered sulfur-containing heterocycle. Preferably X is H and W is OH; or X and W form a carbonyl group.

According to a specific aspect of this first embodiment of this invention, preferably probes of this invention are those in which ring A is a five-membered ring containing a sulfur atom, as represented by the formulae IIa and IIb:

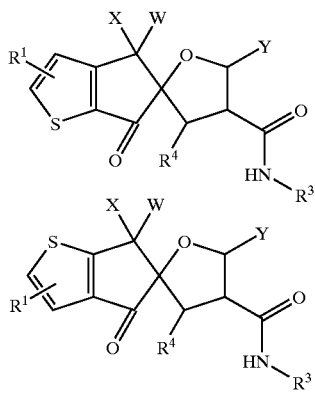

wherein X, W, Y, $R^1$, $R^3$, and $R^4$ are as defined above and wherein said probe binds to the transactivation domain of HPV-11 E2 and is capable of being displaced by a potential inhibitor thereof.

The probes of formulae IIa and IIb exists in forms (1), (2) and (3), as described for the compounds of formula I. Particularly preferred compounds of the invention are compounds having the formula IIa.

With respect to all compounds defined above:

Preferably $R^1$ is a lower alkyl group. More preferably, $R^1$ is methyl.

More preferably, X and W form a carbonyl group.

Preferably, Y is a phenyl group optionally mono- or di-substituted with lower alkyl or halo. More preferably, Y is phenyl substituted with $R^5$ wherein $R^5$ is one or two substituents selected from: Cl or Br.

Preferably, $R^3$ is aryl substituted with a fluorescent label, a chemiluminescent label, or a radioactive label.

Preferably, $R^4$ is a carboxyl group.

More preferably, the probe of the invention has the following formula:

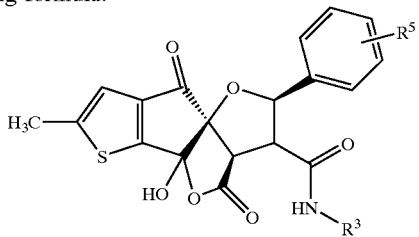

wherein $R^3$ and $R^5$ are as defined above and wherein said probe binds to the transactivation domain of HPV-11 E2 and is capable of being displaced by a potential inhibitor thereof.

More preferably, $R^3$ is phenyl substituted with —$CH_2$—NH—C(O)—$R^{3A}$ or —($CH_2$)—NH—C(S)—$R^{3A}$ wherein $R^{3A}$ is a tritiated —$CH_3$, a fluorescent label or a chemiluminescent label.

Most preferably, $R^5$ is two Br substituents.

More preferably, the molecule is labeled with a radioactive label at any suitable position. As will be readily understood by a person skilled in the art, a radioactive label can be incorporated within the probe of formula I at any suitable position. For example, a $^3H$, or $^{14}C$ isotope can replace any hydrogen or carbon present in the molecule. Similarly, a $^{125}I$ isotope can be substituted on any aromatic ring.

Most preferably, $R^3$ is selected from the group consisting of:

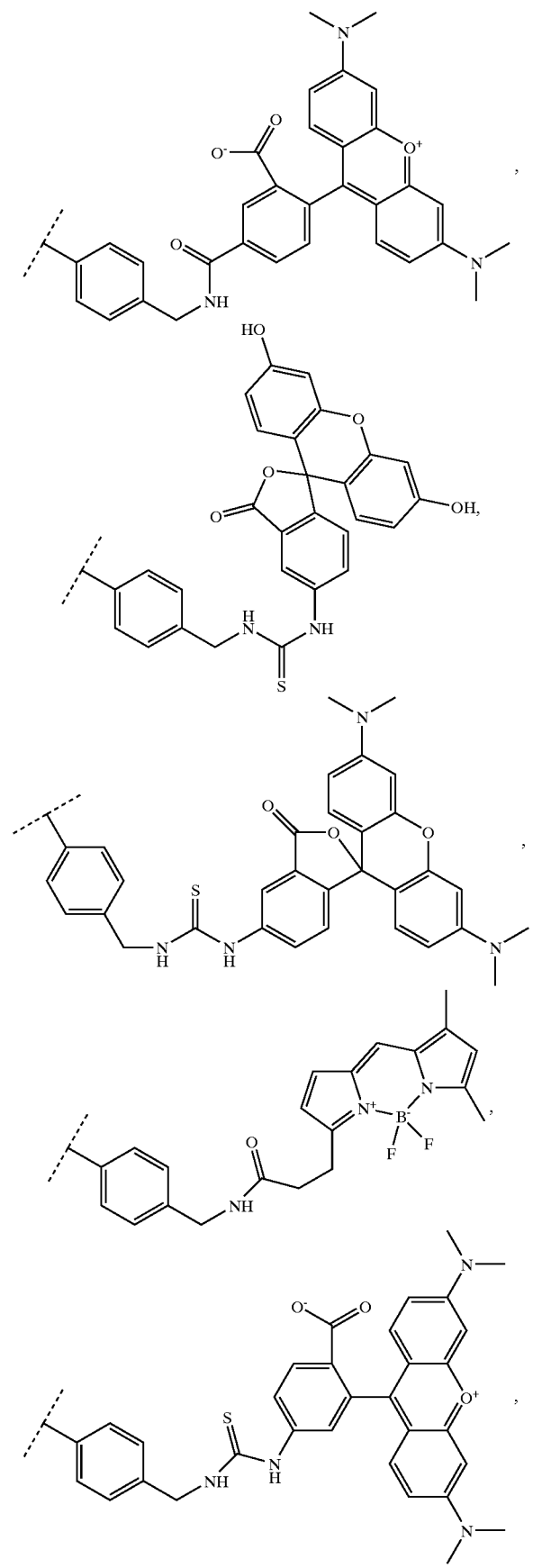

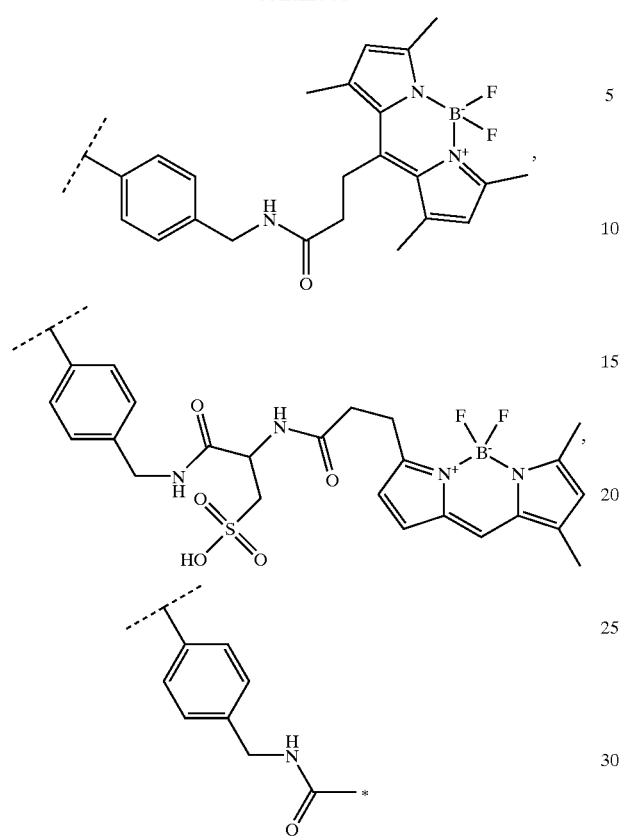
* represents a tritium label,   and
Still, most preferably, R³ is
Specifically, according to a first aspect of the invention, the probe of the present invention is selected from the group consisting of:

-continued
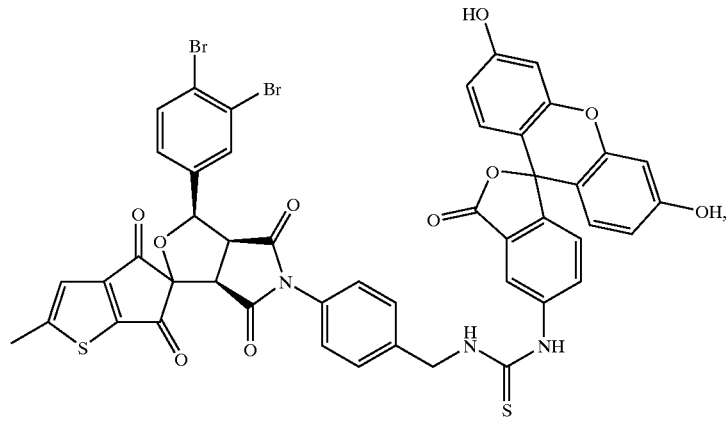
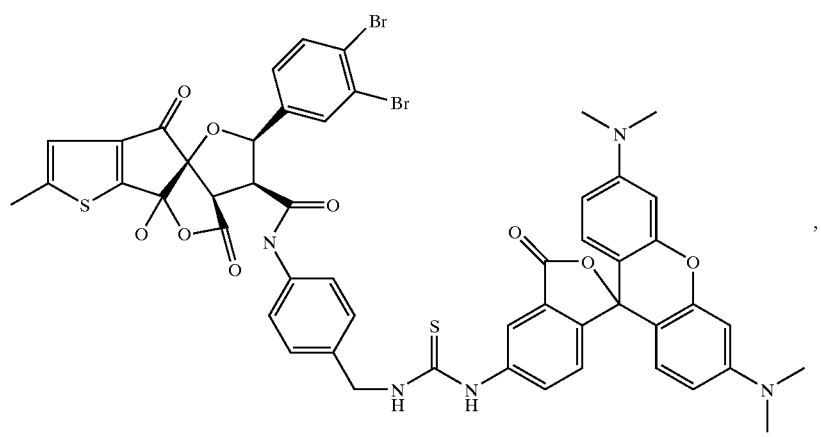
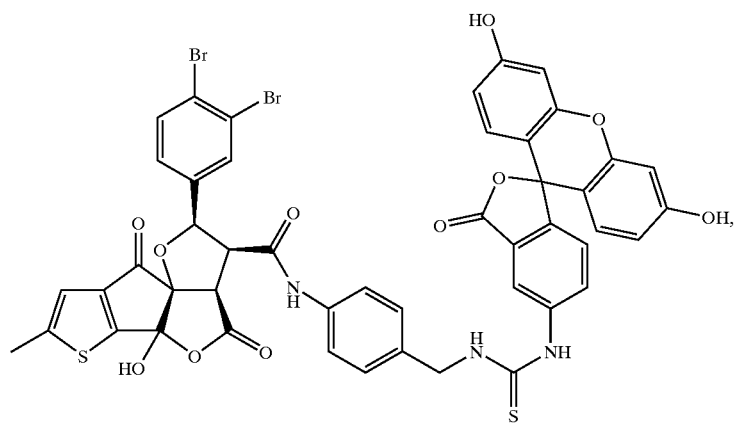
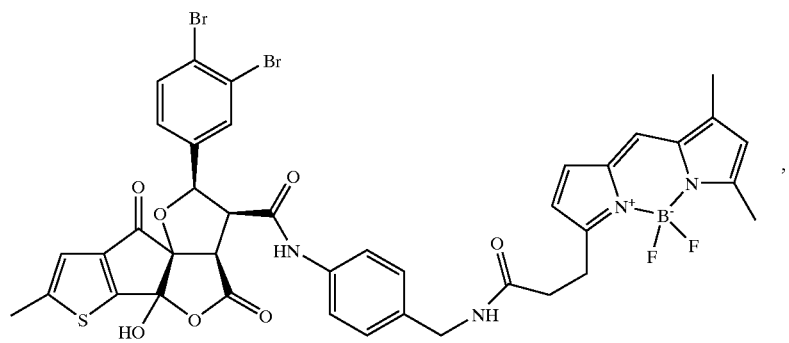

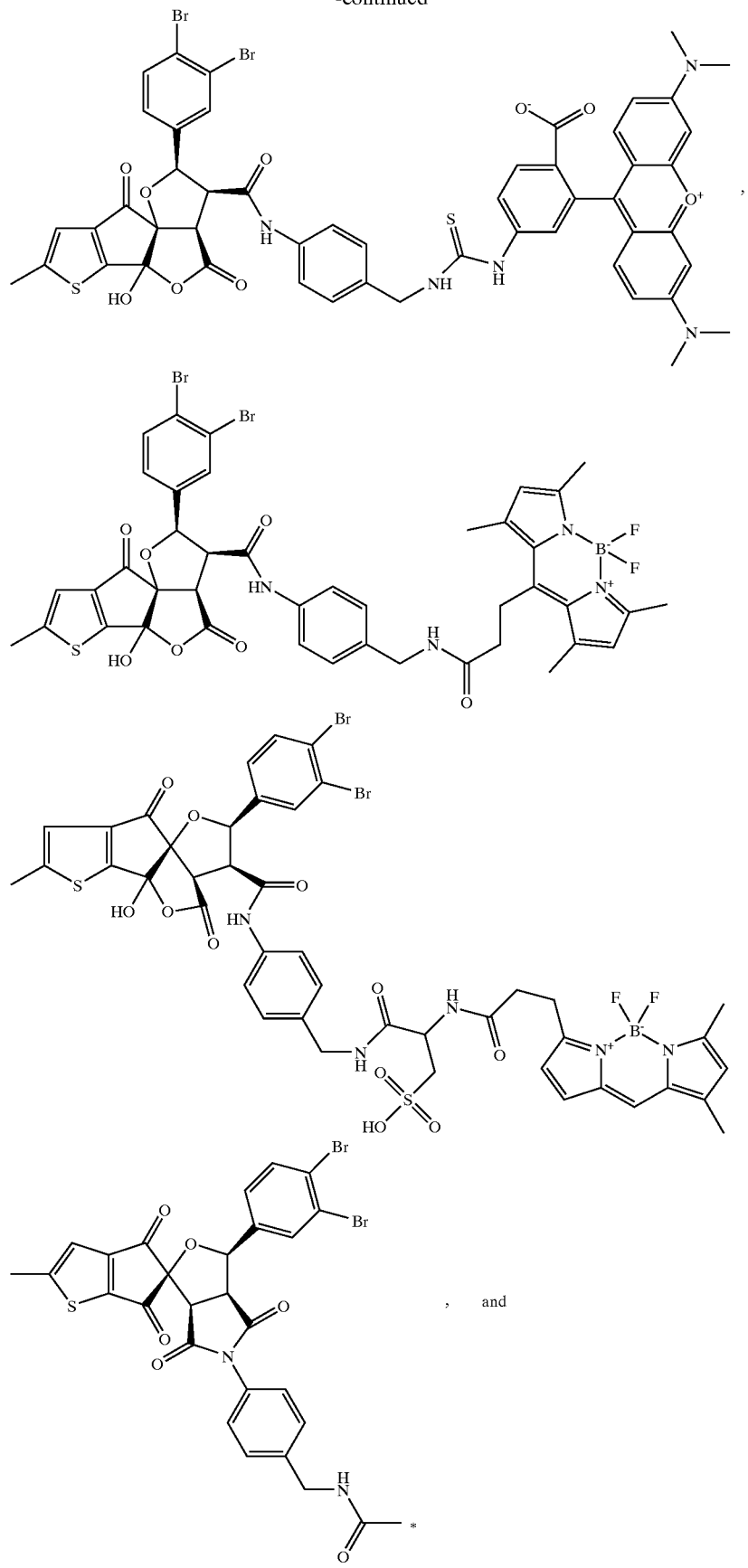

-continued

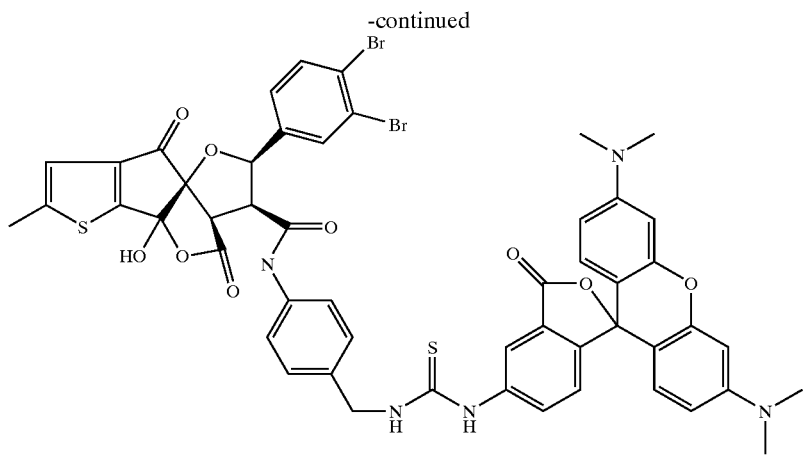

E2 TAD

Preferably, the HPV E2 TAD used in the assay of the invention may be part of the full length HPV E2 protein as described in the state of the art. Alternatively, the E2 TAD is isolated by molecular biology technique and may contain other amino acid sequences at its N-terminal or C-terminal as long as the TAD is capable of binding to the probe of the invention. More preferably, the E2 TAD used in the assay of this invention comprises amino acids 1–190 of the full length E2 protein. Most preferably, the E2 TAD used in the assay of this invention is defined in SEQ ID NO. 1 or SEQ ID No. 5.

The HPV E2 TAD used in the assay may comprise an affinity tag by which the HPV E2 TAD can be attached to a solid support, and the probe may be labeled so as to provide a detectable signal. An example of an affinity tagged E2 TAD is defined by SEQ ID NO. 2.

According to a preferred aspect of this second embodiment, the E2 protein may be obtained from low-risk HPV, preferably from HPV-6 and -11, and most preferably from HPV-11.

Assay

The assay as defined by the present invention may be carried out with different detection methodology depending on the detectable label which preferably may be chosen among: fluorescent label, chemiluminescent label, colorimetric label, enzymatic marker, and radioactive isotope.

As will be understood by a person skilled in the art, the association of a specific probe of the invention with the transactivation domain of HPV E2 can be measured directly or indirectly in a variety of ways. The probe and the transactivation domain of HPV E2 need not be labeled and affinity tagged respectively. The association of a specific probe with the transactivation domain of HPV E2 can be monitored and quantified directly by a change in the intrinsic spectral properties of a tagged or un-tagged HPV E2 domain and/or by a change in the intrinsic spectral properties of a specific probe. A direct measurement of inhibitor-HPV E2 domain association can also be achieved by immobilizing one of these two components on a matrix and measuring association through plasma-resonance detection technology. An assay that quantifies probe-HPV E2 domain complex association may also incorporate a photo-reactive label (such as a phenyl-azide or benzophenone) on the probe and measure the amount of label irreversibly bound to the HPV E2 domain (adduct) following photo-activation of the probe. The label incorporated into the probe may be biotin that is used to indirectly measure the association of this biotinylated probe to the transactivation domain of HPV E2 through the secondary use of an avidin-coupled detection technique. Labels incorporated into the probe may be paired with appropriate labels attached to the tagged transactivation domain of HPV E2 such that the close proximity of the two pairs of labels upon probe-transactivation domain of HPV E2 association results in a measurable signal; examples of such detection techniques include, but are not limited to, fluorescence resonance energy transfer (FRET), and time resolved fluorescence (TRF).

Preferably, when using a fluorescent label in the present assay, the fluorescent label may be selected from: fluorescein, Oregon green, dansyl, rhodamine, Texas-red, phycoerythrin and $Eu^{3+}$.

Alternatively, a fluorescent reporter and quencher may be used as pair of labels to monitor association of the probe with the HPV E2 domain. Commonly known reporter/quencher pair may be selected from, for example: EDANS/DABCYL, tryptophan/2,4-dinitrophenyl, tryptophan/DANSYL, 7-methoxycoumarin/2,4-dinitrophenyl, 2-aminobenzoyl/2,4-dinitrophenyl and 2-aminobenzoyl/3-nitrotyrosine.

Preferably, a chemiluminescent label used in the present assay may be luciferase.

In principle, these tracer methodologies can easily be adapted for the purpose of high-volume screening. Scintillation proximity assay (SPA) methods for radioactive detection have been developed which do not require a separation step and are easily adapted for robotics and microtiter plate format.

Preferably, the radioactive isotope may be selected from: $^3H$, $^{14}C$, and $^{125}I$.

Non-radioactive detection methods have become increasingly widespread in screening assay because of the costs associated with radiolabeled reagents and their disposal. Fluorescence spectroscopy is one of the most prevalent non-radioactive detection methods. One type of assay in which fluorescence may be used is fluorescence polarization. Polarization is independent of total fluorescence intensity; therefore, this technique may not be as prone to interference as fluorescence amplitude measurements.

Preferably, the E2 transactivation domain of the present assay may comprise an affinity tag which in turn comprises a ligand whose strong affinity for a receptor is used to extract from a solution the entity to which said ligand is attached. More preferably, the ligand is selected from: biotin, an amylose sugar moiety and a defined epitope recognizable by a specific antibody.

EXAMPLES

The present invention is illustrated in further detail by the following non-limiting examples. All reactions were performed in a nitrogen or argon atmosphere. Temperatures are given in degrees Celsius. Solution percentages or ratios express a volume to volume relationship, unless stated otherwise.

Abbreviations or symbols used herein include:

DEAD: diethyl azodicarboxylate; DIEA: diisopropyl-ethylamine; DMAP: 4-(dimethylamino)pyridine; DMSO: dimethylsulfoxide; DMF: dimethylformamide;

ES MS: electron spray mass spectrometry; Et: ethyl; EtOAc: ethyl acetate; Et$_2$O: diethyl ether; HPLC: high performance liquid chromatography;e iPr: isopropyl; Me: methyl; MeOH: methanol; MeCN: acetonitrile; Ph: phenyl; TBE: tris-borate-EDTA;

TBTU: 2-(1H-benzotriazol-1-yl)-N,N,N',N'-tetramethyluronium tetrafluoroborate;

TFA: trifluoroacetic acid; THF: tetrahydrofuran; MS (FAB) or FAB/MS: fast atom bombardment mass spectrometry; HRMS: high resolution mass spectrometry.

Example 1

Preparation of Compound 1H

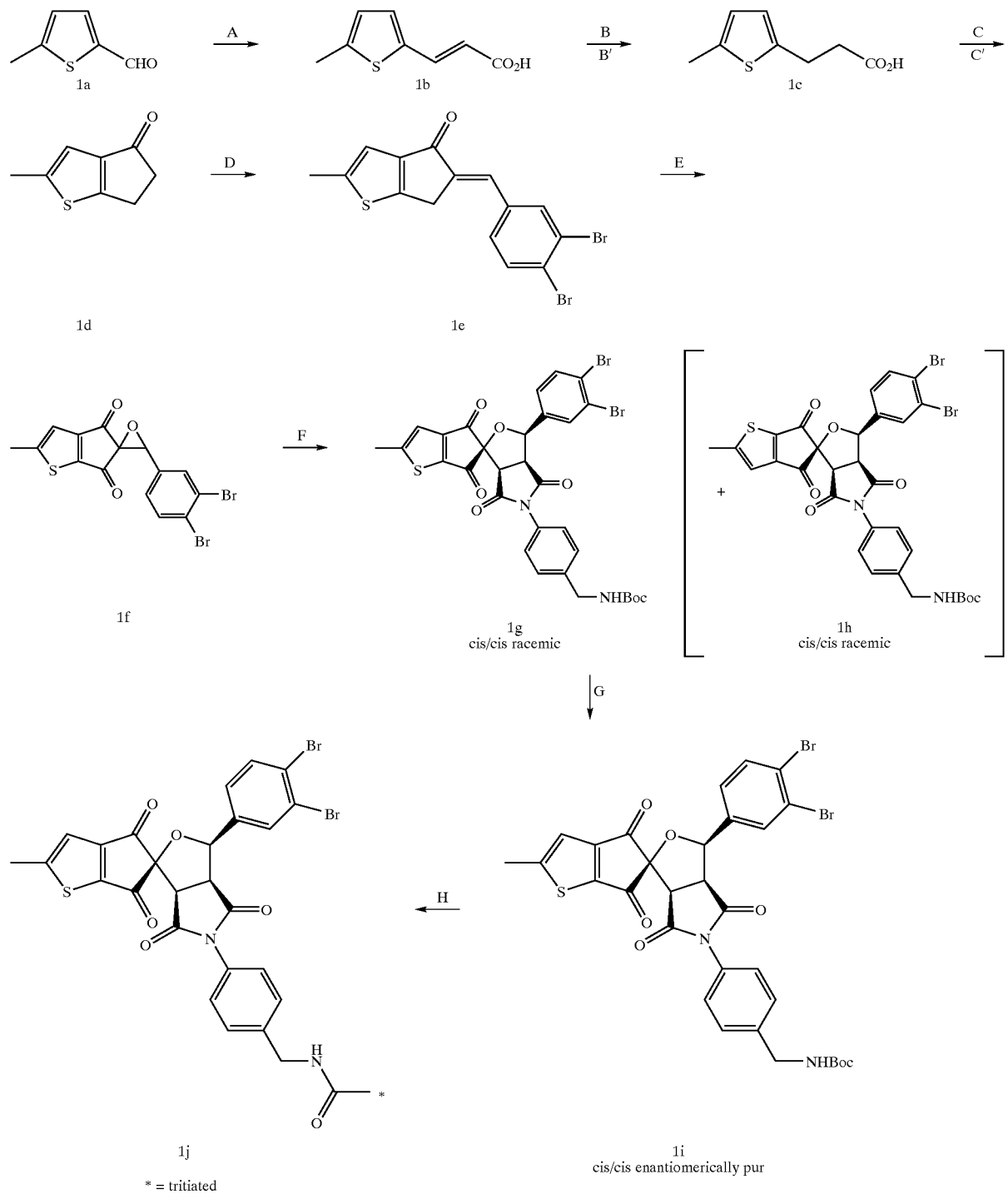

A: A solution of 1a (9.5 g, 75.4 mmol), malonic acid (15.7 g, 151 mmol) and piperidine (1.3 ml) in pyridine (40 ml) was refluxed overnight. The resulting mixture was allowed to cool to room temperature whereupon water (200 ml) was added. The mixture was acidified by the addition of concentrated HCl and allowed to stir for 1 h. The mixture was filtered and the solid washed with water. Drying under vacuum gave 1b as a yellow powder (12.8 g, 100%).

B: To a vigorously stirred solution of 1b (5.9 g, 35 mmol) and 1 N NaOH (46 mL, 46 mmol) in water (40 mL) was added 2% sodium amalgam (82 g, 105 mmol) in small portions over 1 h. After complete addition the mixture was stirred for a further hour. Mercury was removed by decanting and the aqueous solution was acidified with concentrated HCl. Solid NaCl was added to saturation and the resulting mixture was extracted with ether. The combined etherial extracts were washed with brine and dried over $MgSO_4$. Removal of solvent under reduced pressure gave 1c as a brown solid (3.72 g, 62 %).

B': Alternatively, a slurry of 1b (7.5 g, 44.6 mmol) and $Pd(OH)_2$ (500 mg) in ethanol was stirred under an atmosphere of hydrogen for 18 h. Filtering through glass microfibre and removal of solvent gave 1c as a white solid (7.0 g, 93 %).

C: To a solution of 1c (1.75 g, 10.3 mmol) and oxalyl chloride (1.35 mL, 15.4 mmol) in $CH_2Cl_2$ (50 mL) was added one drop of DMF. The resulting solution was stirred at room temperature for 2 h. The solvent was then removed under reduced pressure and the resulting residue dissolved in $CS_2$ (50 mL). Solid $AlCl_3$ (2.05 g, 15.4 mmol) was then introduced and the resulting mixture refluxed overnight. Ice (80 g) was then added followed by concentrated HCl (30 mL) and the resulting mixture was stirred for 30 min. Extraction with $CH_2Cl_2$ was followed by washing with 1 N NaOH, brine and drying ($MgSO_4$). Flash chromatography (20% EtOAc in hexanes) gave 1d (272 mg, 17%) as a yellow solid.

C': Alternatively, solid 1c (1.0 g, 5.88 mmol) was added in small portions to warm (75° C.) polyphosphoric acid (8.5 g). Heating was continued at 75° C. for one hour after the addition was complete. Cooling to room temperature was followed by dilution with water and extraction with $CH_2Cl_2$ (3×). The combined organics were dried over $MgSO_4$ and concentrated. Flash chromatography (50% EtOAc in hexanes) gave 1d as a white solid (0.31 g, 35%).

D: A solution of 1d (1.06 g, 6.97 mmol), 3,4-dibromobenzaldehyde (1.84 g, 6.97 mmol) and p-toluenesulfonic acid (100 mg) in benzene (25 mL) was refluxed for 24 h with azeotropic removal of water. Upon cooling and addition of ether (25 mL) a solid precipitated which was filtered to give 1e as a tan solid (1.35 g, 49%).

E: To a solution of $CrO_3$ (50 mg, 0.50 mmol) in $CH_2Cl_2$ (15 mL) was added tert-butylhydroperoxide (2.6 mL of a 70% solution in water). After stirring for 2 minutes, 1e (1.0 g, 2.51 mmol) was added. After stirring for 18 h at room temperature the solution was diluted with $CH_2Cl_2$ and water and extracted three times with small portions of $CH_2Cl_2$. The combined organics were dried over $MgSO_4$ and concentrated in vacuo. Trituration of the resulting solid with ether gave 0.61 g (60%) of a solid diketone. The material so obtained (0.45 g) was dissolved in EtOH (15 mL) to which was added 30% $H_2O_2$ (0.38 mL) and one drop of 1 N NaOH. After stirring for 3h the solution was filtered to give 1f as a yellow solid (421 mg, 90%).

F: A solution of 1f (5.1 g, 12 mmol) and [4-(2,5-dioxo-2,5-dihydro-pyrrol-1yl)-benzyl]-carbamic acid tert-butyl ester (3.6 g, 12 mmol) in xylene (225 mL) was heated to 145° C. for 48 h. After cooling to room temperature, the reaction mixture was the evaporated to dryness. The resulting residue was purified by fash chromatography ($CHCl_3$:EtOAc, 1:1) to provide a mixture of compounds 1g (974 mg, 11%) and 1h (928 mg, 10%).

G: Racemic 1g (785 mg; was separated on preparative HPLC (multiple injections) using a chiral column (Chiracel OD, isocratic eluent 65% $CH_3CN/H_2O$ containing 0.06% THA; UV lamp at 205 nm; flow 7 m/min) to give pure enantiomer 1i (the most polar isomer; 343 mg, 44%).

H: To a solution of 1i (8.0 mg, 11 mmoles) in dry methylene chloride (3.0 mL, EM Science lot 41046), was added 0.8 mL of 4 M HCl in 1,4-dioxane (Aldrich lot DO 06914 CO) at 0 C. The ice bath was removed and the reaction was warmed to room temperature and stirred for 2 hours. Thin layer chromatography showed no starting material. The solvents were removed under a stream of nitrogen and methylene chloride (2.0 mL) was added to the reaction vial. The solvent was evaporated again under nitrogen to chase excess of HCl. The residue was further dried under reduced pressure. The product (HCl salt) was then suspended in ethyl acetate (1.0 mL) and triethylamine (0.1 mL, Aldrich lot EO 12909 PI) was added followed by N-acetoxyphthalimide [acetoxy-$H^3$] (80 mCi, specific activity 20 Ci/mmol, American Radiolabeled Chemicals, Inc. Lot 010730) in ethyl acetate (3.0 mL). The reaction was stirred at room temperature for 3 hours before cold N-acetoxyphthalimide (0.9 mg, 4.38 μmoles, batch 5272-131, prepared according to M. Saljoughian, H. Morimoto, P. G. Williams, C. Than, and S. J. Seligman. J. Org. Chem. 1996, 61, 9625–9628) was added with triethylamine (0.05 mL). The reaction was further stirred for 30 minutes. The solvents were removed under a stream of nitrogen and the solid residue was purified by flash chromatography (silica gel packed in a Pasteur pipette) using ethyl acetate: hexane (1:1) as eluent. The product 1j was obtained as a white solid (3.0 mg) with a specific activity of 9.2 Ci/mmol and a total activity of 41 mCi or 51% radiochemical yield.

Radio-HPLC (mobile phase: gradient water: acetonitrile, both contain 10 mM TFA, from 95% water to 100% acetonitrile in 30 minutes; Zorbax® SB-C18 column, 3×150 mm, UV detection at 220 nm) and TLC-Bioscan (10% Ethanol: ethyl acetate as eluent of the TLC plate) were used to confirm the identity of the product.

Example 2

Preparation of Compound 2c

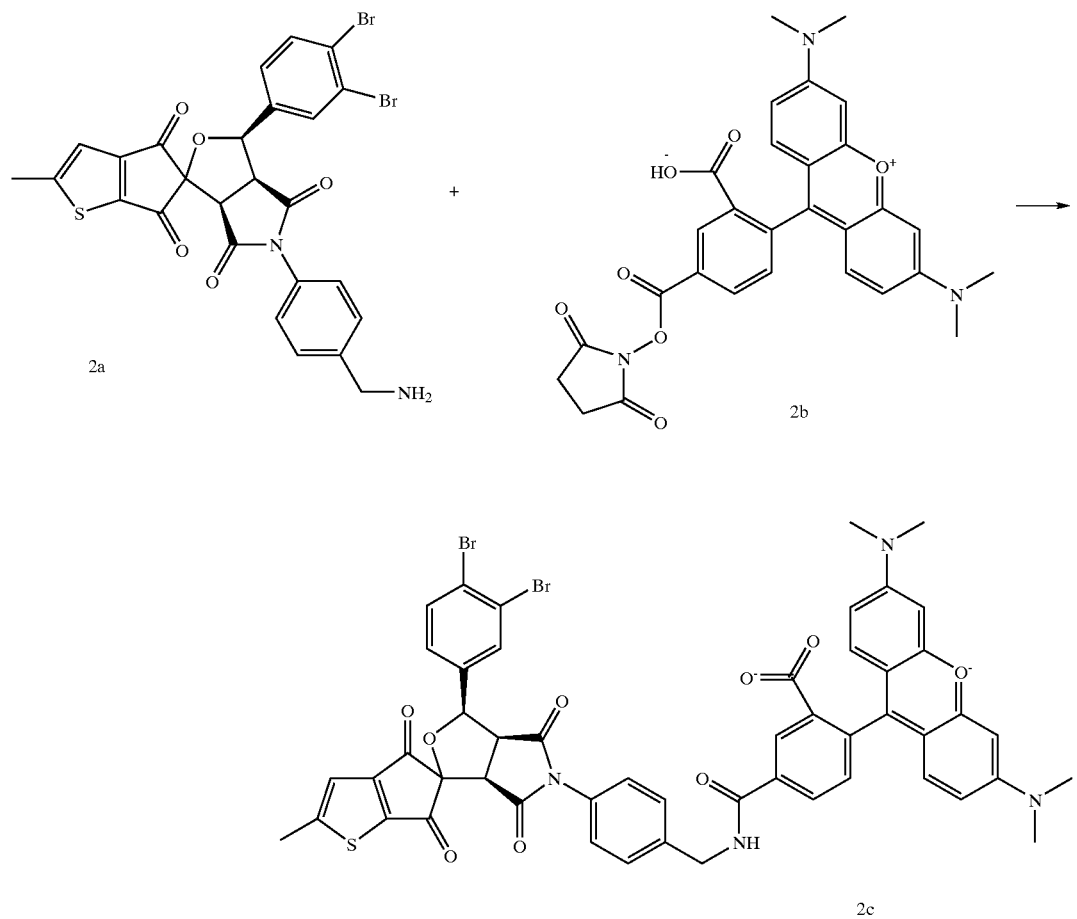

To a stirred solution of 2a (9 mg, 0.017 mmol, prepared from 1i according to step H above) and (2b)TAMRA-SE (Molecular Probes) (9 mg, 0.017 mmol) in DMF (1 mL), DIPEA (5 μL, 0.029 mmol) was added. The resulting clear red mixture was stirred for 1.5 hours at room temperature. Purification by HPLC (A:0.1% TFA/H$_2$O; B:0.1% TFA/75% MeCN, 25% H$_2$O; gradient % B=30 to 20 over 60 min.) furnished 2c (11.9 mg, 83% yield) as a red solid. M/z (MH$^+$ 104.1).

Example 3

Preparation of Standard Inhibitor Compound 3H

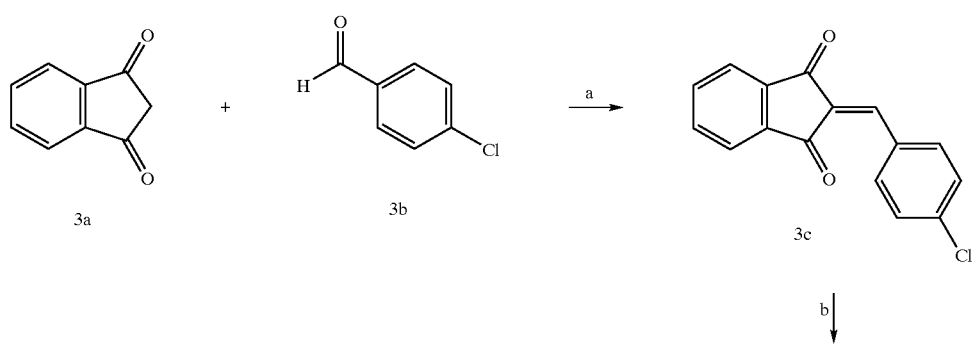

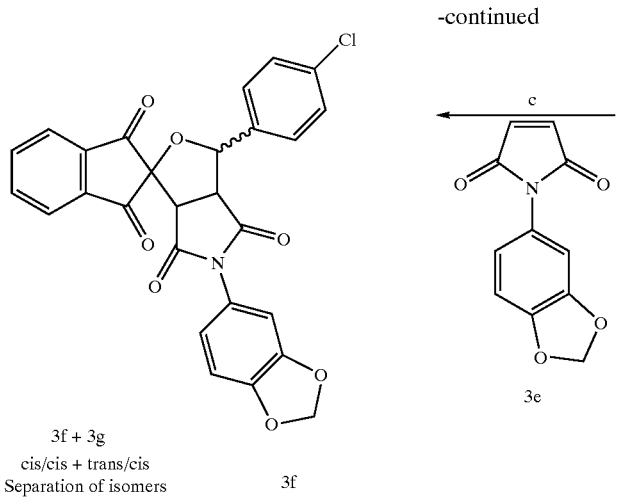

3f + 3g
cis/cis + trans/cis
Separation of isomers          3f

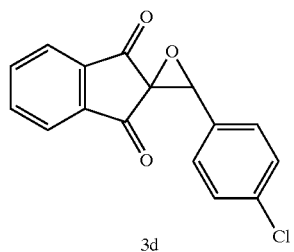

3e

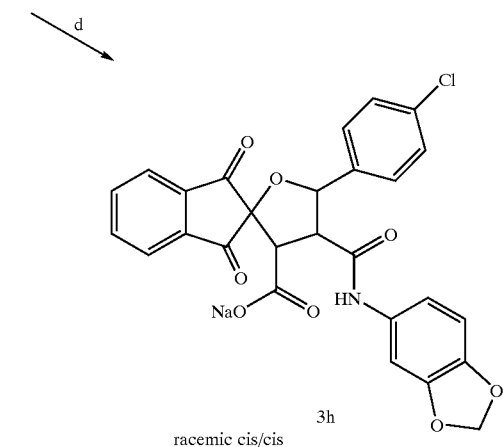

3h
racemic cis/cis

Step a: To a solution of indan-1,3-dione (3a) (960 mg, 6.6 mmol) in EtOH (8.2 mL) was added 4-dichlorobenzaldehyde (3b) (1.3 g, 7.2 mmol) followed by piperidine (3 drops). The reaction mixture was heated at reflux for 30 min. After cooling, the reaction was diluted with EtOH (8 mL) and the precipitate was filtered. The resulting solid was triturated twice with EtOH and dried under high vacuum to give 2-(4-chloro-benzylidene)-indane-1,3-dione (3c) (1.7 g, 82% yield).

Step b: To a suspension of 2-(4-chloro-benzylidene)-indane-1,3-dione (3c) (1.6 g, 5.2 mmol) in MeOH (13 mL) was added hydrogen peroxide (30% solution, 3 mL). The mixture was cooled to 0° C. and sodium hydroxide (1N, 300 μL) was added dropwise. After addition was completed, stirring was continued at room temperature for 1 h. The mixture was then poured into water (5 mL) and the resulting solid was collected by filtration and washed with water and MeOH. After drying under high vacuum 3-(3,4-dichlorophenyl)-spiro (oxirane-2,2'-indan)-1',3'-dione (3d) (1.6 g, 95% yield) was obtained.

Step c: A mixture of 3-(4-chlorophenyl)-spiro (oxirane-2,2'-indan)-1',3'-dione (3d) (11 g, 33.4 mmol) and 1-benzo (1,3) dioxol-5-yl-pyrrol-2,5-dione (3e) (7.3 g, 33.4 mmol) in toluene (167 mL) was heated to reflux for 16 h. After cooling and concentration, the residue was purified by flash chromatography (SiO₂, gradient 50% EtOAc/hexane to 30% hexane/EtOAc) to give compound 3f (cis/cis isomer, 17.9 g, 50% yield) and (3g) (trans/cis isomer, 4.1 g, 23% yield).

Step d: To a solution of 3f (143 mg, 0.27 mmol) in CH₃CN (27 mL) was added NaOH (0.02N, 135 mL, 0.27 mmol) using a syringe pump over 1 h. After the addition was completed, the reaction mixture was stirred for an extra 2 h and the resulting solution was concentrated and lyophilized to give compound 3h (161 mg, 100% yield) as a white solid.

Example 4

Expression and Purification of the HPV-11 E2 Transactivation Domain

The first 215 amino acids of HPV-11 E2 (SEQ ID NO.1) were subcloned by PCR from a pCR3 plasmid containing the full-length gene for HPV11 E2, using the primers 5'-GCG GCG GGA TCC GM GCA ATA GCC MG CGT TTA GAT G-3' (SEQ ID NO.3) and 5'-GCG GCG CTC GAG GGT GTA TGT AGT AGG TTC AGC AAT G-3' (SEQ ID NO.4). The product was cleaved with BamHl and Xhol then ligated into plasmid pET23a(+). The resulting construct contains an N-terminal epitope tag from the N-terminus of the phage T7 major capsid protein and a C-terminal polyhistidine tag to facilitate purification using metal affinity chromatography. Recombinant plasmid was transformed into *E. coli* strain BL21 (DE3)pLysS (Novagen). For expression, Circle Grow medium (Bio 101, Inc) containing 100 μg/mL ampicillin and 34 μg/mL chloramphenicol was inoculated with one-fiftieth volume of a fresh overnight culture and cells were grown at 37° C. until an O.D. (600 nm) of approximately 0.6 was reached. The culture was then shifted to 15° C. and protein expression was induced with 0.5 mM isopropylthiogalactoside. Cells were harvested after 16 hours by centrifugation and frozen on dry ice.

All purification steps were carried out at 4° C. Cells were resuspended at 5 mL per gram in lysis buffer (25 mM Tris pH 8.0 (measured at r.t.), 500 mM NaCl, 5 mM TCEP plus protease inhibitors 1 mM Pefabloc, 1 mM PMSF, and 2.5 μg/mL each antipain, leupeptin, and pepstatin A), then sonicated. The crude lysate was centrifuged for 30 min at 2500 g. The supernatant was filtered through a 0.8 μM Millex-PF filter (Millipore). Chromatographic purification was performed using a Pharmacia FPLC system equipped with a UV detector. A 5 mL Hi-Trap chelating column was charged with Nickel sulfate and equilibrated with purification buffer A (same as lysis buffer above but with 2 mM TCEP and no protease inhibitors). Buffer B was the same as buffer A except for the inclusion of 500 mM imidazole. Filtered supernatant was loaded onto the column, which was then washed with buffer A until detector absorbance decreased to background levels. The column was then washed with 30–35 mL at 5% buffer B (25 mM imidazole). A linear gradient from 5–50% buffer B was then run, and E2 TAD eluted at approximately 25%. TAD-containing fractions were concentrated to approximately two mL and loaded onto a size-exclusion column (Hi load 16/60 Superdex 75 (Pharmacia), incorporated into a similar FPLC system) equilibrated with buffer A. TAD-containing fractions from this column were pooled, giving a final yield of approximately 29 mg/L of culture.

SEQ ID NO. 5 comprising the approximate "minimal" E2 trans-activation domain (amino acids 1–195) was also subcloned in a similar fashion, appropriately tagged, and used in the assay with satisfactory results.

Example 5

HPV E2 Transactivation Domain (TAD) Ligand Displacement Assay

This assay measures the binding of a radiolabeled compound ("probe") to the transactivation domain of HPV11 E2 (TAD). The protein binds to Ni-coated Flash plates, and the measured signal being proportional to the concentration of bound probe. If a test compound binds to the TAD, it will displace the probe, which will result in a lower signal.

Radiolabeled probe: The tritium labeled probe 1j binds to the TAD with a $K_d$ of 40 nM, as determined by isothermal titration calorimetry with its non-tritiated homolog.

HPV-11 TAD: HPV11 E2 amino acids 2* -215 (*Met-1 removed) with an amino terminal epitope tag derived from the T7 phage gene 10 protein and a C-terminal His tag (SEQ ID NO.2). Total MW is 27 kDa.

Standard inhibitor 3h: $IC_{50}$ approximately 10 μM (racemic mixture):

| | Stock Solutions | | | | |
|---|---|---|---|---|---|
| | [] | weigh | H$_2$O | pH | storage |
| MOPS-NaOH | 1.0 M | 209.3 g | to 1 L | 7.0, r.t. | 4° C. |
| DTT | 1.0 M | 1.54 g | to 10 mL | — | −20° C. |
| NaCl | 5.0 M | 292.2 g | to 1 L | — | r.t. |
| Tween-20 | 10% v/v | 1 mL | to 10 mL | — | r.t. |

All solutions should be made using distilled, deionized water and filtered through 0.45 μM filters.

Other Materials

DMSO; Ni Chelate Flashplates (Perkin Elmer; 96-well= SMP107 (pkg of 5) & 384-well=SMP412A (pkg of 10))

Assay Buffer (Used for Compounds, Protein, and Probe): 25 mM MOPS, pH 7.0; 100 mM NaCl; 1 mM DTT; 0.0025% Tween-20. The pH was verified before adding DTT and Tween, and was adjusted where necessary. Alternatively, 0.5 mM TCEP can be used in place of DTT (adjust pH after adding TCEP). The solution was then filtered.

Preparation of Assay Solutions

1. Compound Solutions

Compounds were diluted to 30 μg/mL in assay buffer plus 6% DMSO. 6% DMSO/94% buffer was used for blanks and controls. For the standard inhibitor (3h), the buffer was made up to 30 μM (10 μM in the assay). The method used 20 μL per well, therefore in the assay, compounds were in 2% DMSO/98% buffer.

2. TAD Solutions

TAD was diluted to 300 nM in assay buffer and used 20 μL E1 dilution per well. Final concentration was 50 nM. Blanks may be run either with (60 μL total volume) or without (40 μL total volume) an extra 20 μL buffer to make up the final volume. Blanks are slightly lower if the extra buffer is added. This has a measurable effect on signal: background but little effect on z' or measured inhibition (J.-H. Zhang, et al., 1999, J. Biomolecular Screening v4(2), 67–73).

3. Probe Solution

The probe was diluted to 75 nM, in the assay buffer, to give a final concentration of 25 nM in the assay. The method used 20 μL per well. The total volume for the binding reaction is 60 μL for both 96-well and 384-well plates.

Example 6

Typical Procedure for E2 TAD Ligand Displacement Assay ($IC_{50}$ Curve)

The assay was performed in 96-well FlashPlates (PE/NEN). Plates were pretreated by incubating with 200 μL/well (96-well plates) water containing 0.0025% v/v Tween®-20 detergent. Typically, two one hour incubations were performed; this pretreatment was found to decrease assay background and also stabilizes the signal after long incubation times. Assay buffer, adjusted to pH 7.0, contained MOPS (25 mM), NaCl (100 mM), TCEP (0.5 mM) and Tween-20 (0.0025% v/v). Assays were run in a final volume of 60 μL, containing 20 μL each of test compound, T7 epitope-tagged HPV11 E2-TAD, and tritiated probe {[$^3$H] solutions (added to pretreated plates in the order given). Test inhibitor was dissolved to three-fold over test concentrations in assay buffer plus 6% DMSO (2% DMSO in assay). Test concentrations ranged from 80 to 0.33 μM, in 3-fold dilutions. E2-TAD and radiolabeled probe were diluted to 150 nM and 50 nM, respectively, in assay buffer (50 nM and 25 nM, respectively, in the final assay). Positive controls, containing E2 TAD and probe but no test inhibitor, and negative controls, containing only probe, were run in some wells. Control volumes were adjusted to 60 μL with assay buffer and DMSO to 2% final concentration. Plates were then sealed with TopCount-compatible sealing film, shaken briefly, incubated at room temperature, then counted on the TopCount after 3 hrs and again at 20 hrs.

Example 7

E2 Ligand Displacement Assay at Different Salts and Salt Concentrations

E2 ligand displacement assay was carried out in different concentrations of NaCl or KCl. This assay was run in a 96-well plate under similar conditions as defined above, except that the final assay volume was 100 μL and the buffer consisted of 25 mM HEPES, 0.005% IGEPAL CA-630 in place of Tween-20 (pH 7.5), plus the indicated salt concentration. 1 mm DTT was used as the reducing reagent. Salt concentrations ranged from 25 to 200 mm. FIG. 1 shows results obtained for NaCl (A) and KCl (B), with data shown for blanks containing only probe (white), positive controls with probe and TAD (black), and wells containing a standard inhibitor 3h (gray).

Example 8

E2 Ligand Displacement Assay at Different pH

Figure 2:
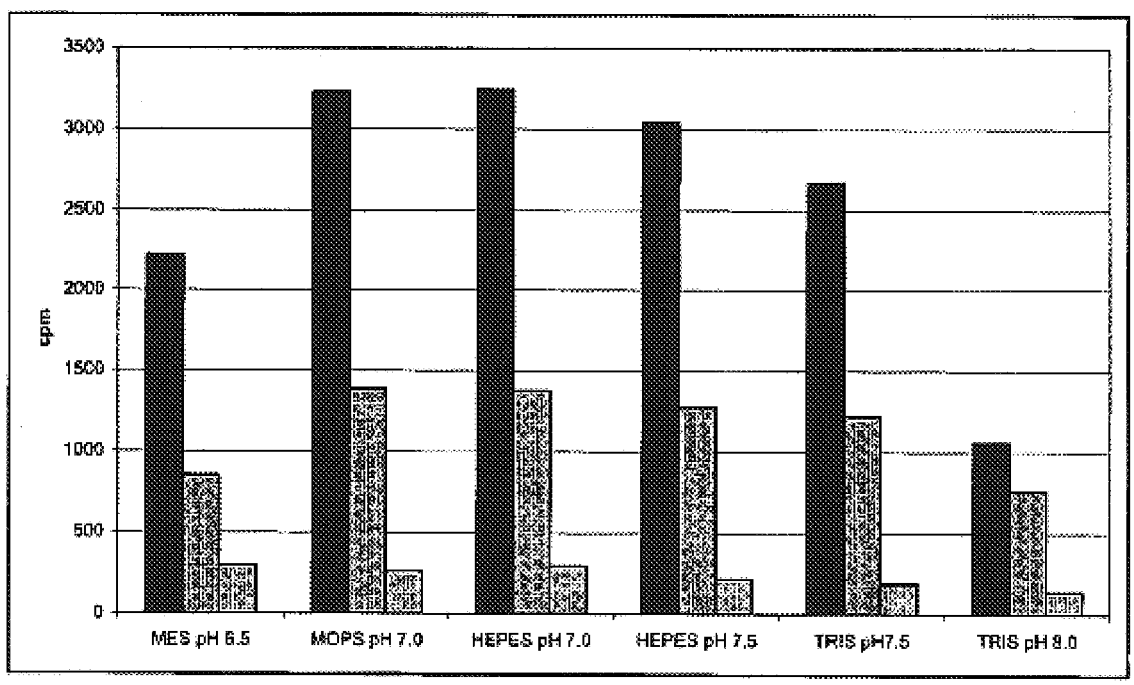
FIG. 2 shows a graph of a ligand displacement assay carried out using different buffers adjusted to pH values between 6.5 and 8.0. Shown are cpm obtained for wells with TAD and probe (black), for wells with a standard inhibitor added (dark gray), and wells with probe but no TAD (light gray)

This assay was run in a 96-well plate under the conditions described in Example 6, except that the assay volume was 90 µL (30 µL each component), and TAD and radiolabeled probe concentrations were 100 nM and 50 nM, respectively. 1 mM DTT was used as the reducing reagent. Assay buffer composition was similar to that described, but with the stated buffer used at 25 mM. Shown in FIG. 2 is data for wells with probe and TAD (black), probe only (light gray) and probe, TAD, and a standard inhibitor 3h (dark gray).

Example 9

Titration of Probe and TAD in The E2 Ligand Displacement Assay

Figure 3A:
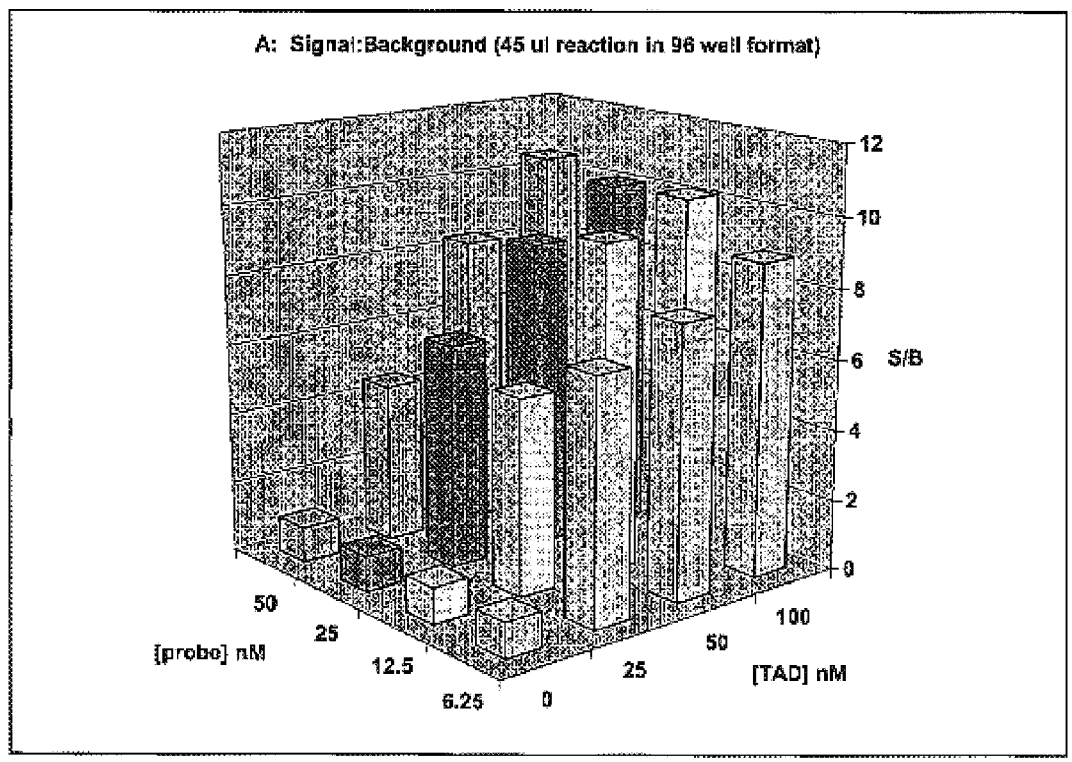
FIG. 3 shows a graph of titration of TAD and probe. A) signal: background ratio obtained using TAD concentrations from 0–100 nM and probe concentrations from 6.25 to 50 nM; and B) activity for wells with a standard inhibitor relative to wells with TAD and probe but no inhibitor.
Figure 3B:
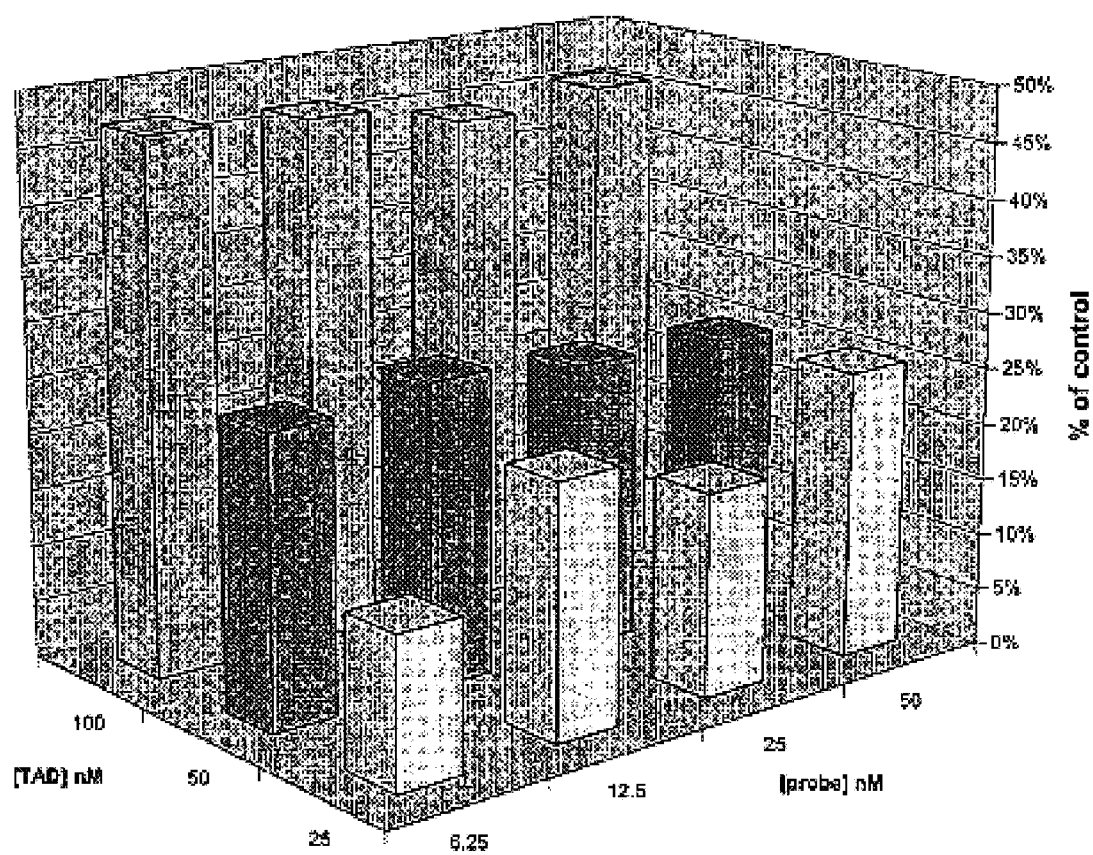

This assay was run in a 96-well plate under the conditions described in Example 6, except that the assay volume was 45 µL (15 µL each component), and TAD and radiolabeled probe concentrations were varied as shown in FIG. 3. 1 mM DTT was used as the reducing reagent. FIG. 3A shows that signal: background ratios increase significantly up to 50 nM, and only slightly for 100 nM. Ratios are not affected by the probe concentrations, though the absolute cpm increases in proportion to the radiolabel concentration. FIG. 3B shows that the signal from wells with 100 nM TAD is significantly less affected by the standard inhibitor 3h, indicating that some of the signal is nonspecific. From this experiment, concentrations of 50 nM for TAD and 25 nM for probe were chosen as preferred.

Example 10

E2 Ligand Displacement Assay Under High-Throughput Conditions

Figure 4:
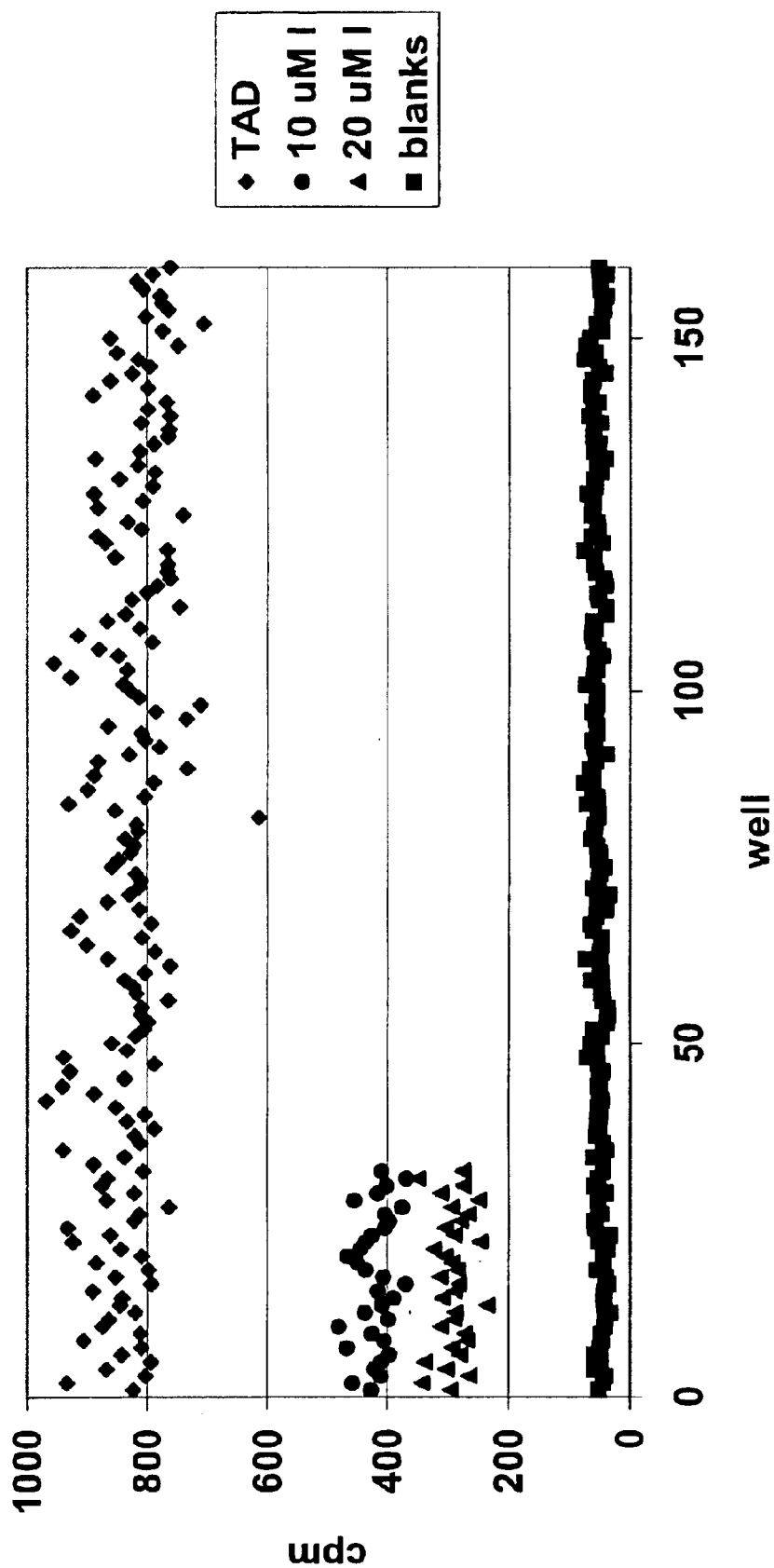
FIG. 4 shows a graph of an assay carried out under screening conditions to show the reproducibility of results. Graphed are cpm obtained for wells with TAD and probe (diamonds), wells with 10 μM (circles) or 20 μM (triangles) of a standard inhibitor, and wells with probe but no TAD (squares)

This assay was run in a 384-well plate under the conditions described in Example 6, except that the assay volume was 45 µL (15 µL each component), and TAD and radiolabeled probe concentrations were 100 nM and 50 nM, respectively. 1 mM DTT was used as the reducing reagent. The plate was counted after a 5 hour incubation and results are shown in FIG. 4. Wells A1-P10 contained probe only, no TAD (squares). Wells A11-P20 contained probe and TAD (diamonds). Wells A21-H24 contained standard inhibitor 3h at 20 µM (triangles), and wells I21-P24 contained the same compound at 10 µM (circles).

Example 11

$IC_{50}$ Curves

Figure 5:
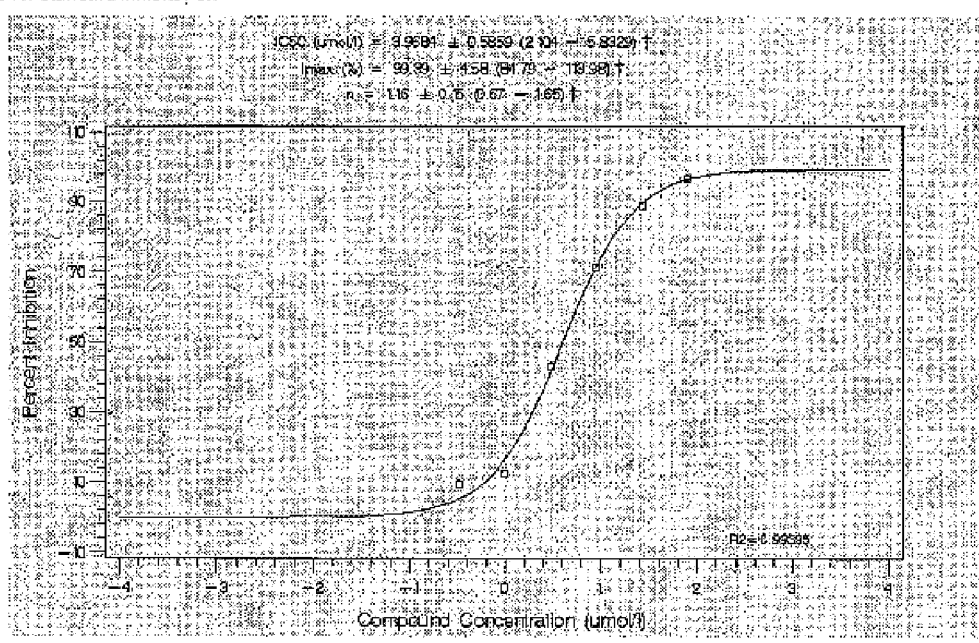
FIG. 5 shows a typical $IC_{50}$ curve for standard inhibitor (3h).

The assay was run as described in Example 6. For each inhibitor concentration, the percent inhibition observed was calculated and the resulting inhibition curve was fit to a logistic using SAS. The curve obtained after counting at 20 hours gave an $IC_{50}$ value of 4.0±0.6 µM (FIG. 5). Similar results were observed after three hours incubation.

Example 12

Validation Using the E2-Dependent E1 DNA Binding Assay

This assay was modeled on a similar assay for SV40 T Antigen described by McKay (J. Mol. Biol., 1981,145:471). A 400 bp radiolabeled DNA probe, containing the HPV-11 origin of replication (Chiang et al., 1992, Proc. Natl. Acad. Sci. USA 89:5799) was produced by PCR, using plasmid pBluescript™ SK encoding the origin (nucleotides 7886-61 of the HPV-11 genome in unique BAMH1 site) as template and primers flanking the origin. Radiolabel was incorporated as [$^{33}$P]dCTP. Binding assay buffer consisted of: 20 mM Tris pH 7.6, 100 mM NaCl, 1 mM DTT, 1 mM EDTA.

Other reagents used were protein A-SPA beads (type II, Amersham) and K72 rabbit polyclonal antiserum, raised against a peptide corresponding to the C-terminal 14 amino acids of HPV-11 E1 . Following the protocol from Amersham, one bottle of beads was mixed with 25 mL of binding assay buffer. For the assay, a saturating amount of K72 antiserum was added to the beads and the mixture was incubated for 1 h, washed with one volume of binding assay buffer, and then resuspended in the same volume of fresh binding assay buffer. Binding reactions contained 8 ng of E2, approximately 100–200 ng of purified E1 , and 0.4 ng of radiolabeled probe 1j in a total of 75 µL of binding assay buffer. After 1 h at room temperature, 25 µL of K72 antibody-SPA bead suspension was added to the binding reaction and mixed. After an additional hour of incubation at room temperature, the reactions were centrifuged briefly to pellet the beads and the extent of complex formation was determined by scintillation counting on a Packard Top-Count™. Typically, the signal for reactions containing E1 and E2 was 20–30 fold higher than the background observed when either E1 , E2, or both was omitted. The compound tested in Example 11 and also FIG. 5, was also tested in this assay and gave a similar $IC_{50}$ value.

Discussion

E1 and E2 are essential proteins for productive HPV infection, and the direct interaction of E1 with E2 is a critical step for the replication of viral DNA. Thus, inhibitors of this interaction are potential drugs for treatment of HPV disease.

To ease the identification of inhibitors of this critical protein-protein interaction, we have developed an assay in which an N-terminal subdomain of the E2 protein (E2 TAD) interacts with labeled inhibitors of the E1–E2 protein-protein interaction (as determined by the E2-dependent E1-DNA binding assay described in Example 12). Since a probe inhibitor is labeled with either a radioactive or fluorescent substituent, displacement of the probe by test molecules is easily observed as a decrease in the scintillation or fluorescence signal measured in an appropriate instrument. We have reasoned that other small molecules which displace the probe inhibitor from the E2 TAD would themselves be inhibitors of the E1–E2 protein-protein interaction, and thus potential anti-HPV drugs.

The ligand displacement assay described herein overcomes limitations of some previously described assays. E2 TAD has been purified in large quantities from E. coli, and thus is much easier to obtain than the full-length E1 and E2 proteins; labeled probe inhibitors are obtained by straightforward chemical syntheses. As shown in FIG. 1, the assay is quite insensitive to ionic strength, and thus the activity of test compounds can easily be assessed over a wide range of salt concentrations. Similarly, the assay is relatively insensitive to pH over the range from pH 6.5 to 7.5, as shown in FIG. 2. The results in FIGS. 3 and 4 demonstrate that the assay provides an excellent window between signal and background over a wide range of protein and probe concentrations and that the signal is very reproducible, allowing the straightforward identification of compounds which reduce the observed protein-probe interaction. Importantly, it is possible to use this assay to quantitatively evaluate the affinity of test compounds for the E2 TAD, as shown in FIG. 5 for a standard inhibitor. This standard inhibitor has a similar $IC_{50}$ value in the E2-dependent E1-DNA binding assay described in Example 12, and demonstrates that inhibitors identified through this ligand displacement method will also inhibit the E1–E2 protein-protein interaction, and thus are potential anti-HPV drugs.

What is claimed is:

1. An assay for the identification of inhibitors of HPV, comprising:
   a) contacting a HPV E2 transactivation domain with a probe to form a E2:probe complex and measuring a signal from said probe to establish a base line level;
   b) incubating the E2:probe complex with a test compound and measuring the signal from said probe;
   c) comparing the signal from step b) with the signal from step a);

wherein said probe is a compound of formula (I) or its enantiomers or diastereoisomers thereof:

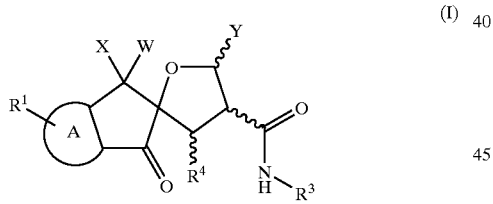

(I)

wherein:

A is a 5- or 6-membered homocyclic ring, or a 5- or 6-membered heterocyclic ring containing 1 or more heteroatoms selected from N, O and S;

X is H and W is OH; or X and W together form a carbonyl group or an epoxide;

$R^1$ is H; or one or two substituents independently selected from the group consisting of: hydroxy, halo, lower alkyl, lower alkoxy, lower thioalkyl, haloalkyl, or —C(O)$R^2$ wherein $R^2$ lower alkyl, alyloxy or benzyloxy;

Y is phenyl optionally mono- or di-substituted with $R^5$ or C(O)$R^6$, wherein $R^5$ is lower alkyl, lower cycloalkyl, lower alkoxy, halo, hydroxy, nitrile or trifluoromethyl, and $R^6$ is lower alkyl, lower cycloalkyl, lower alkoxy, hydroxy or trifluoromethyl;

said phenyl ring being optionally fused with a saturated or unsaturated 4 to 6-membered ring optionally containing a heteroatom selected from N, O and S;

or Y is a heterocycle (Het) containing one or more heteroatom selected from N, O or S, said Het optionally mono- or di-substituted with $R^5$ or C(O)$R^6$, wherein $R^5$ and $R^6$. are as defined above; said Het being optionally fused with a saturated or unsaturated 4 to 6-membered ring optionally containing a heteroatom selected from N, O and S;

or Y is ethylene-phenyl, said ethylene moiety being optionally mono-substituted with lower alkyl, wherein said phenyl ring is optionally mono- or di-substituted with $R^5$ or C(O)$R^6$, wherein $R^5$ and $R^6$ are as defined above; said phenyl ring being optionally fused with a saturated or unsaturated 4- to 6-membered ring optionally containing a heteroatom selected from N, O and S;

or Y is ethylene-Het, said ethylene moiety being optionally mono-substituted with lower alkyl, wherein Het is optionally mono- or di-substituted with $R^5$ or C(O)$R^6$, wherein $R^5$ and $R^6$ are as defined above; said Het being optionally fused with a saturated or unsaturated 4 to 6-membered ring optionally containing a heteroatom selected from N, O and S;

$R^3$ is selected from the group consisting of: lower alkyl, lower cycloalkyl, lower alkylene, aryl or lower aralkyl, all of which optionally mono- or di-substituted with: lower alkyl, lower cycloalkyl, haloalkyl, halo, CN, azido, lower alkoxy, (lower alkyl)acyl, $C^{1-6}$ thioalkyl, $C^{1-6}$ alkylsulfonyl, NHC(O)-lower alkyl, NHC(O)-aryl, NHC(O)—O-lower alkyl, NHC(O)O-aryl, aryl, aryloxy, hydroxy, nitro, amino, or Het, said Het optionally mono- or di-substituted with lower alkyl, lower cycloalkyl, lower alkoxy, halo, hydroxy, nitrile, trifluoromethyl, C(O)$R^6$ wherein $R^6$ is as defined above; said lower cycloalkyl, aryl, lower aralkyl or Het being optionally fused with a saturated or unsaturated 4 to 6-membered ring optionally containing a heteroatom selected from N, O and S; and $R^4$ is a carboxylic acid, a salt or an ester thereof;

and wherein said;

probe of formula (I) is labeled with a detectable label or an affinity tag, wherein wavy lines represent bonds of unspecified stereochemistry; and wherein said signal is selected from: fluorescence, resonance energy transfer, time resolved fluorescence, radioactivity, fluorescence polarization, change in the intrinsic spectral properties, luminescence and plasma-resonance;

whereby a modulation in said signal is an indication that said test compound binds to said transactivation domain.

2. An assay for the identification of inhibitors of HPV replication, comprising:

a) contacting a transactivation domain of HPV E2 protein with a probe of formula I as defined in claim 1, to form an E2:probe complex and measuring a signal from said probe to establish a base line level;

b) incubating a E2 protein with a test compound;

b') adding a probe of formula (I) to said mixture of E2 and test compound from step b) and measuring the signal from said probe; and c) comparing the signal from step a) with the signal from step b');

whereby a modulation in said signal is an indication that said test compound binds to said transactivation domain.

3. The assay according to claim 1, wherein said detectable label is selected from the list consisting of: a fluorescent label, a chemiluminescent label, a colorimetric label, an enzymatic marker, and a radioactive isotope.

4. The assay according to claim 1, wherein said detectable label is a fluorescent label selected from the list consisting of: fluorescein, Oregon green, dansyl, rhodamine, tetramethyl rhodamine, Texas-red, phycoerythrin BODIPY®FL, BODIPY®493/503 and $Eu^{3+}$.

5. The assay according to claim 4, wherein said detectable label is a chemiluminescent label.

6. The assay according to claim 3, wherein said radioactive isotope is selected from the list consisting of: $^3H$, $^{14}C$, and $^{125}I$.

7. The assay according to claim 1, wherein said affinity tag comprises a ligand whose strong affinity for a receptor is used to extract from a solution the entity to which said ligand is attached.

8. The assay according to claim 7, wherein said ligand is selected from the list consisting of: biotin, a poly-histidine peptide and a defined epitope recognizable by a specific antibody.

9. The assay according to claim 1, wherein said probe is a compound of formula (I), present in an "cis/cis" relative stereochemistry represented as follows:

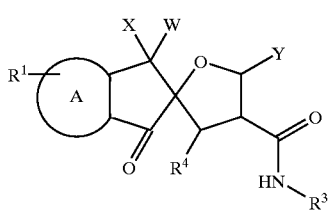

wherein $R^1$ is a lower alkyl group; A is a 6-membered carbocyclic ring or a 5-membered sulfur-containing heterocycle; X is H and W is OH; or X and W form a carbonyl group; Y is an phenyl group optionally mono- or di-substituted with lower alkyl or halo; $R^3$ is aryl substituted with a fluorescent label, a chemiluminescent label, or a radioactive label; and $R^4$ is a carboxyl group.

10. The assay according to claim 9, wherein said probe comprises pure enantiomers of compounds of formula (Ia) or (Ib) with the relative stereochemistry "cis/cis";

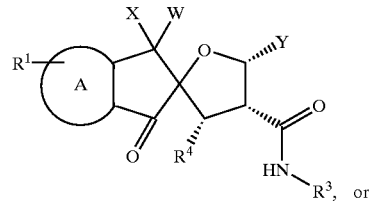

(Ia)

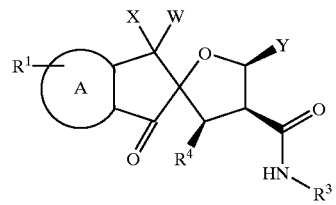

(Ib)

wherein $R^1$, A, X, W, Y, $R^3$ and $R^4$ are as defined in claim 9.

11. The assay according to claim 10, wherein said probe comprises pure cis/cis enantiomers of compounds of formulae IIa and IIb:

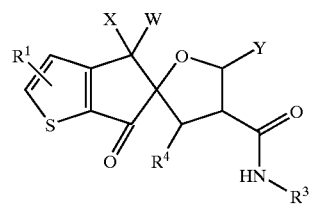

(IIa)

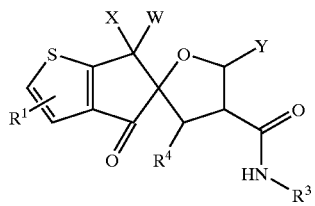

(IIb)

wherein $R^1$ is a lower alkyl group; X and W form a carbonyl group; Y is an phenyl group optionally mono- or di-substituted with lower alkyl or halo; $R^3$ is aryl substituted with a fluorescent label, a chemiluminescent label, or a radioactive label; and $R^4$ is a carboxyl group.

12. The assay according to claim 11, wherein for said probe, $R^1$ is methyl, Y is phenyl substituted with $R^5$ wherein $R^5$ is one or two substituents selected from: Cl or Br; and $R^3$ is phenyl substituted with —$CH_2$—NH—C(O)—$R^{3A}$ or —($CH_2$)—NH—C(S)—$R^{3A}$ wherein $R^{3A}$ is a fluorescent label, a chemiluminescent label, or a radioactive label.

13. The assay according to claim 12, wherein said probe has the following formula:

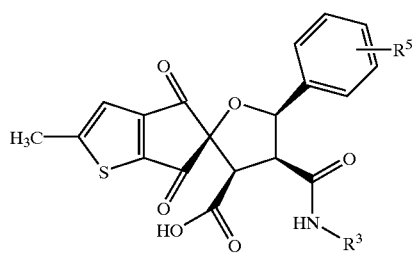
wherein $R^5$ is di-bromo, and $R^3$ is phenyl substituted with —$CH_2$—NH—C(O)—$R^{3A}$ or —($CH_2$)—NH—C(S)—$R^{3A}$ wherein $R^{3A}$ is a tritiated —$CH_3$, a fluorescent label or a chemiluminescent label.
14. The assay according to claim 13, wherein $R^3$ is selected from:
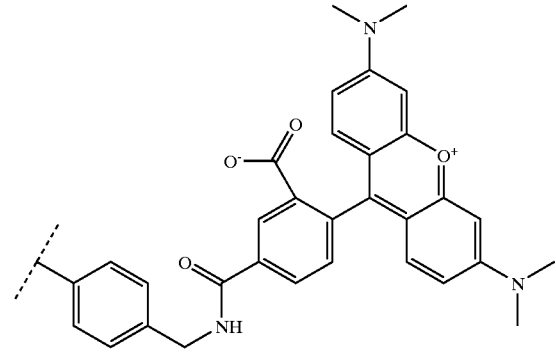
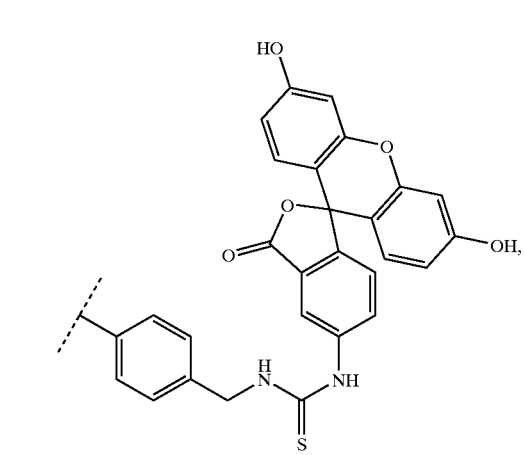
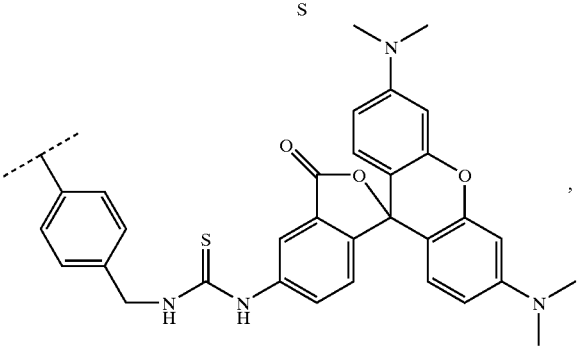
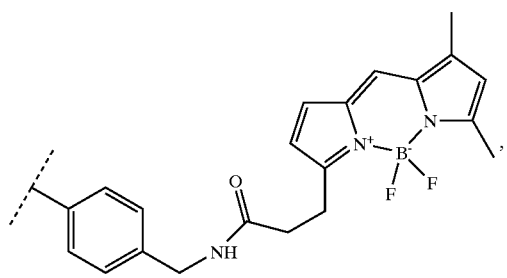
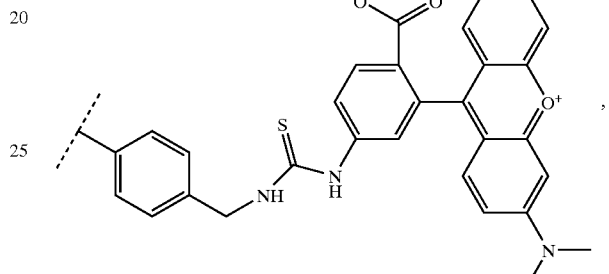
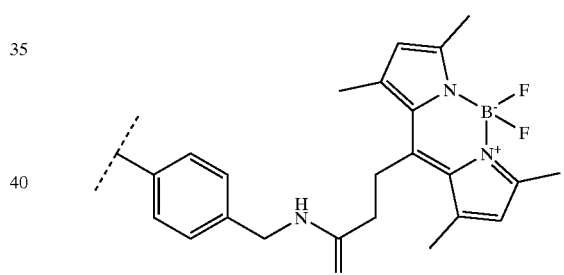
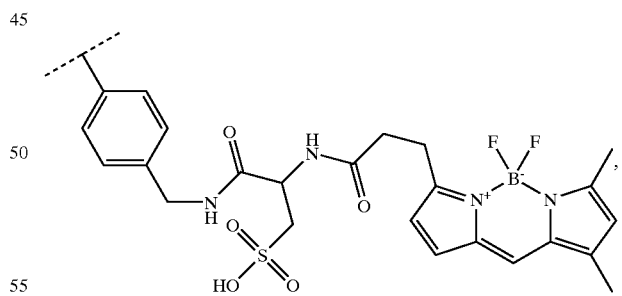
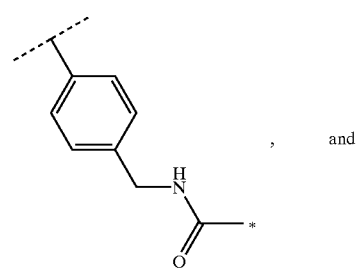
and -continued
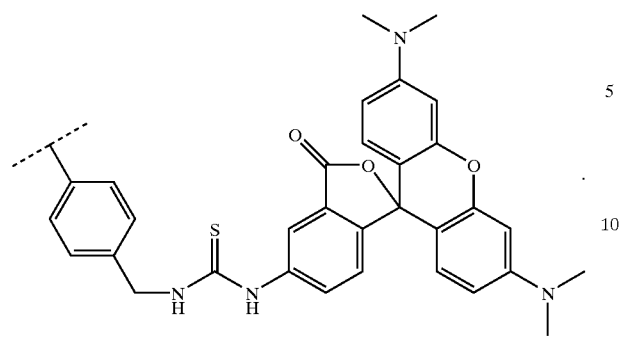
wherein the * represents a tritium label.
15. The assay according to claim 14, wherein said R³ is
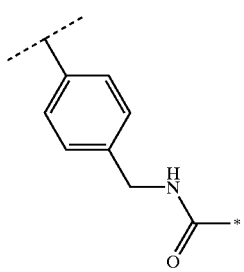
wherein the * represents a tritium label.
16. The assay according to claim 1, wherein said probe is selected from:
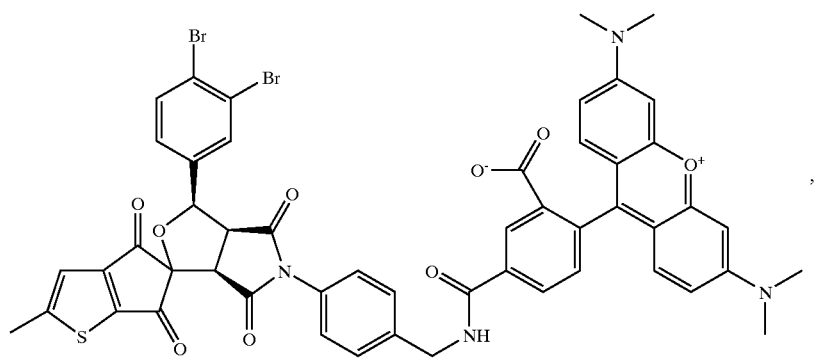
,
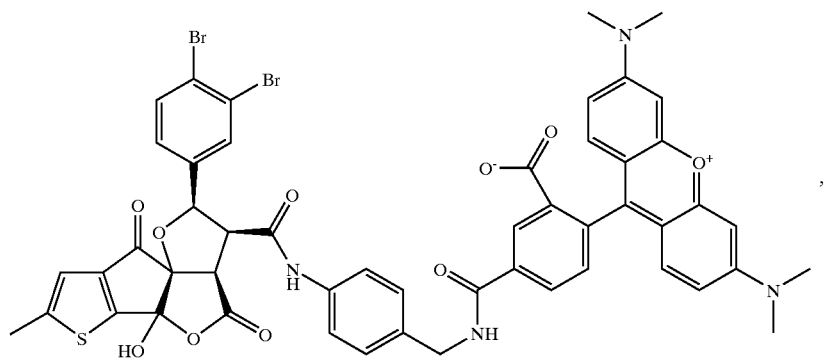
,
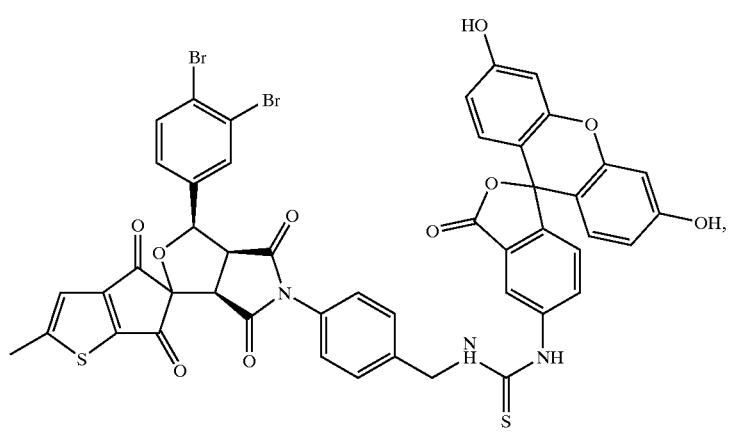

-continued
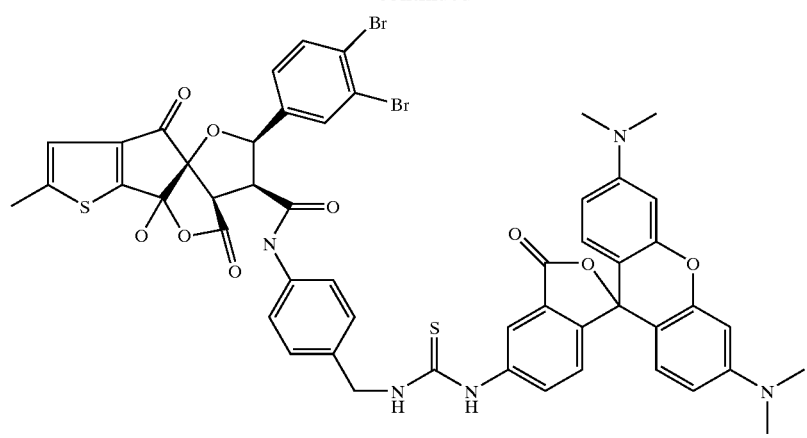
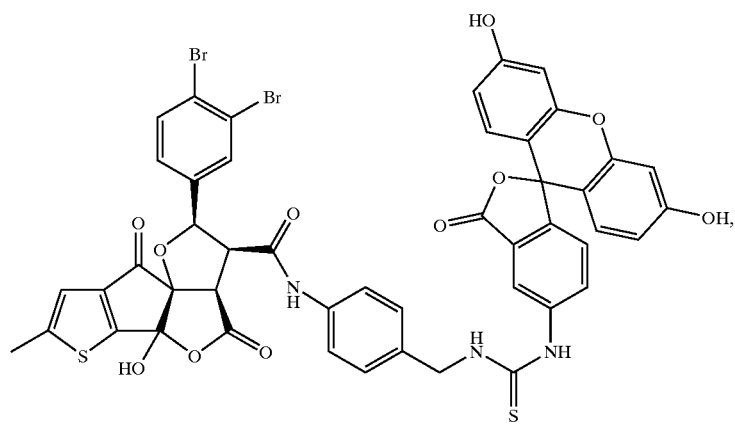
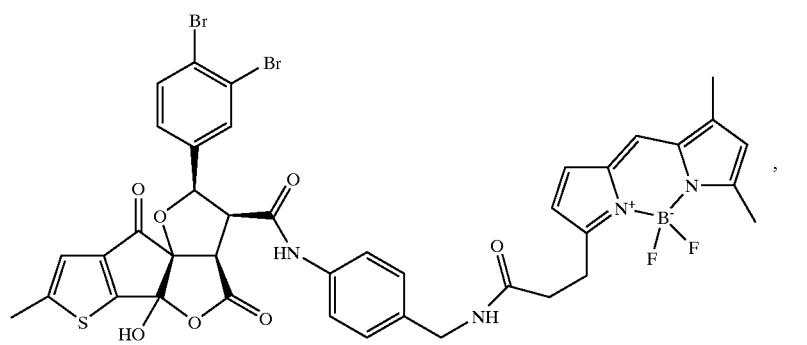
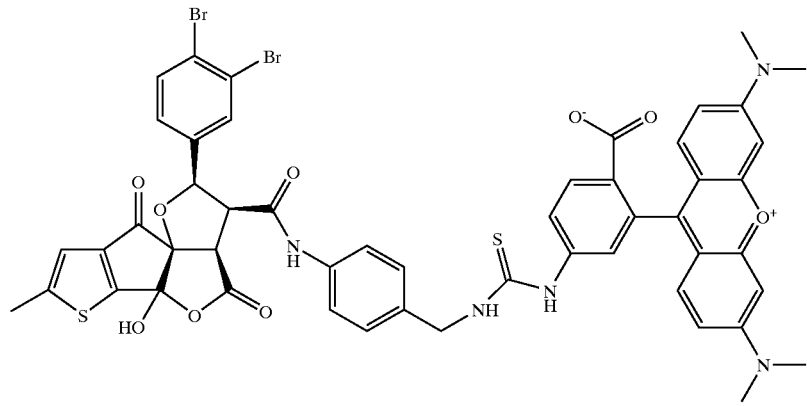

-continued
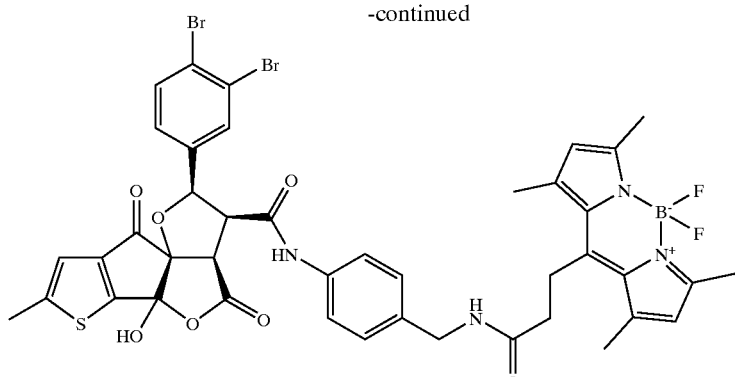
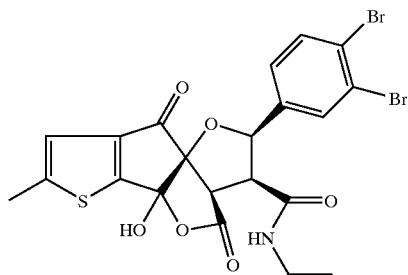
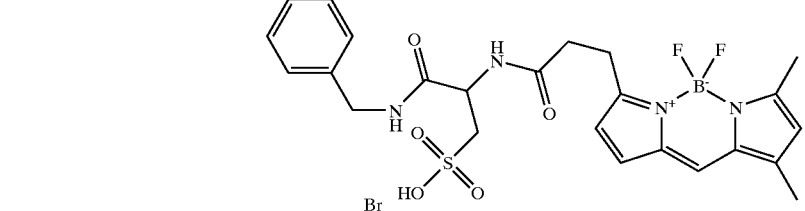
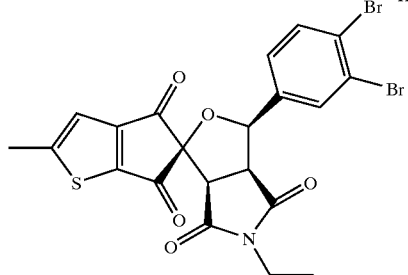
, and
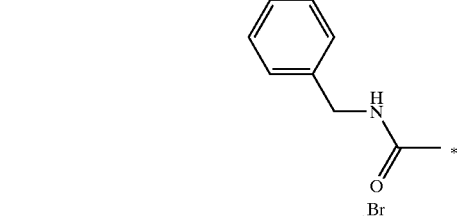
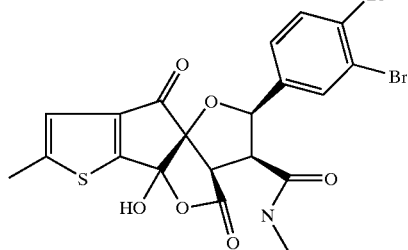

17. The assay according to claim 1, wherein said E2 transactivation domain is selected from the list consisting of: full length E2 protein, a protein comprising amino acids 1–190 of the full length E2 protein, SEQ ID NO.1, SEQ ID NO.2 and SEQ ID NO.5.

18. The assay according to claim 17, wherein said E2 transactivation domain is from a low risk type papillomavirus.

19. The assay according to claim 18, wherein said low risk papillomavirus is selected from: HPV-6 and HPV-11.

20. The assay according to claim 19, wherein said low risk papillomavirus is HPV-11.

21. A probe that binds to the transactivation domain of HPV-11 E2 and is capable of being displaced by a potential inhibitor thereof; said probe having the formula:

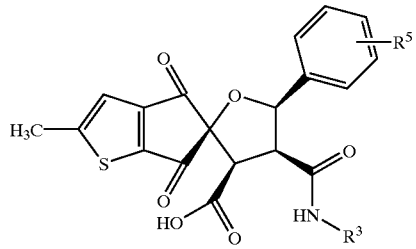

wherein $R^5$ is lower alkyl, lower cycloalkyl, lower alkoxy, halo, hydroxy, nitrile or trifluoromethyl, and $R^3$ is aryl substituted with a fluorescent label, a chemiluminescent label, or a radioactive label.

22. The probe according to claim 21, wherein $R^5$ is one or two halogen substituents.

23. The probe according to claim 22, wherein $R^3$ is phenyl substituted with —$CH_2$—NH—C(O)—$R^{3A}$ or —($CH_2$)—NH—C(S)—$R^{3A}$ wherein $R^{3A}$ is a fluorescent label, a chemniluminescent label, or a radioactive label.

24. The probe according to claim 23, wherein $R^3$ is selected from:

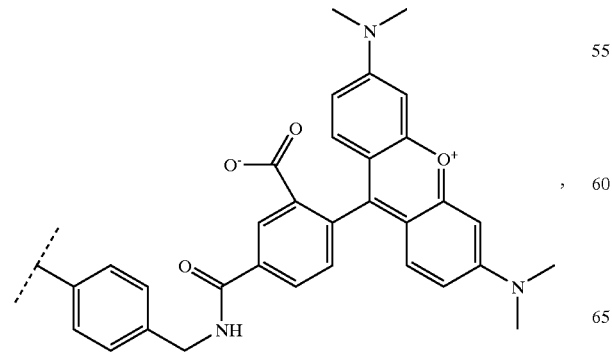

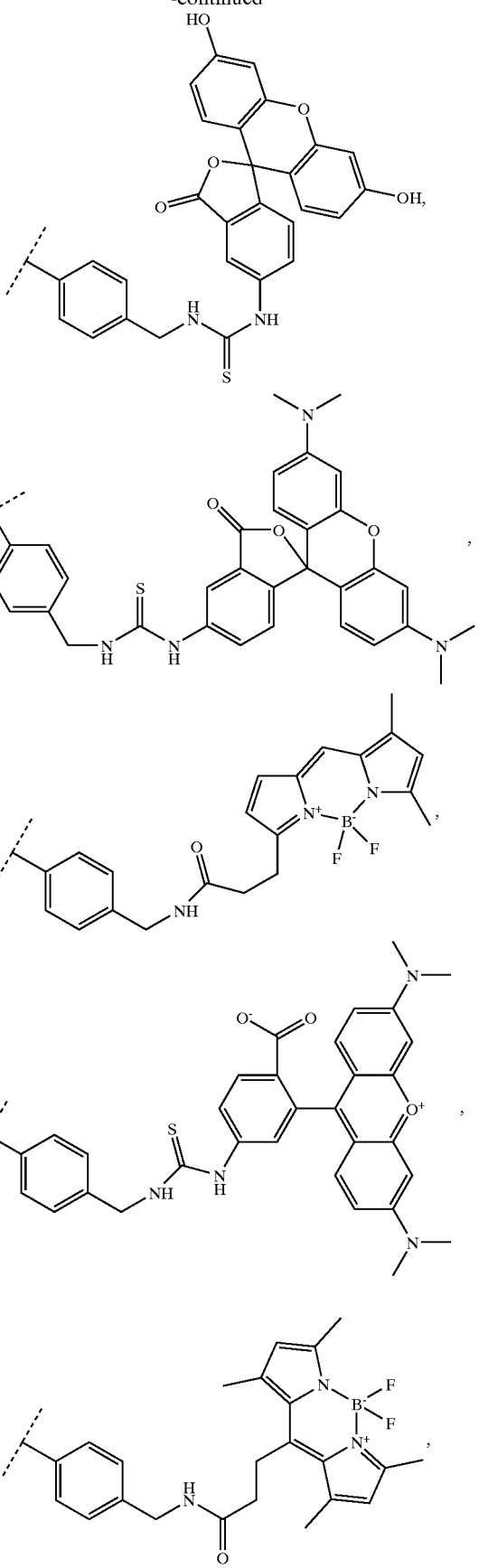

-continued
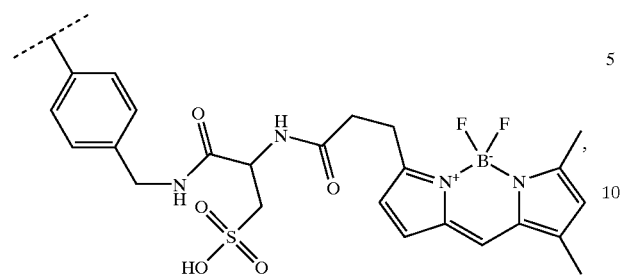
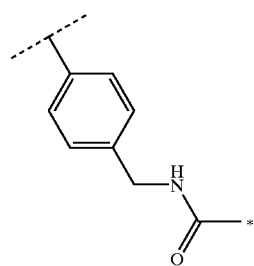
* represents a tritium label, and
-continued
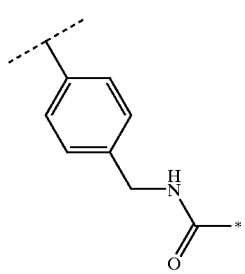
wherein the * represents a tritium label.
25. The probe according to claim 24, wherein said $R^3$ is
wherein the * represents a tritium label.
26. The probe according to claim 21, selected from: invention is selected from the group consisting of:
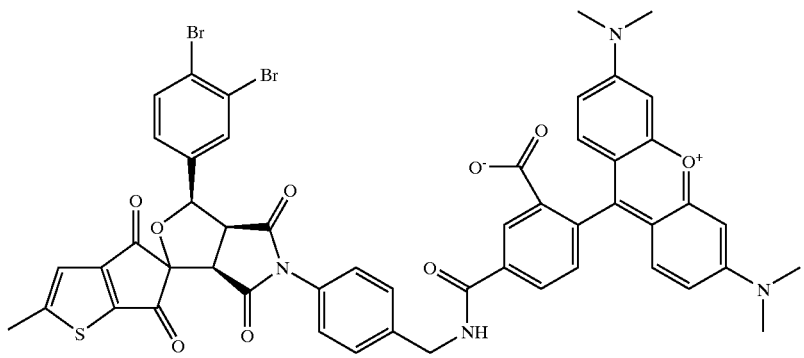
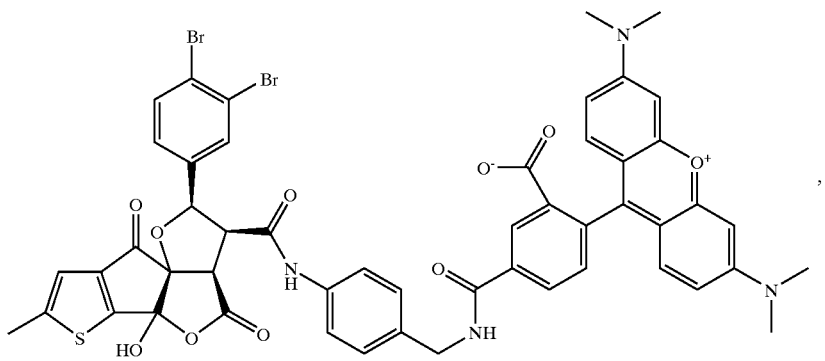

-continued
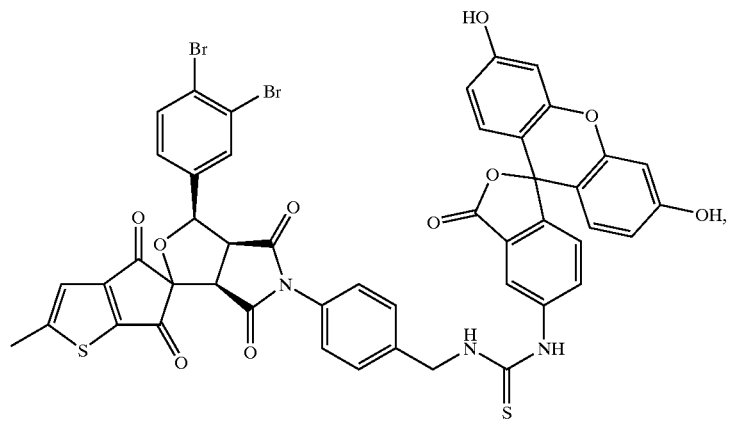
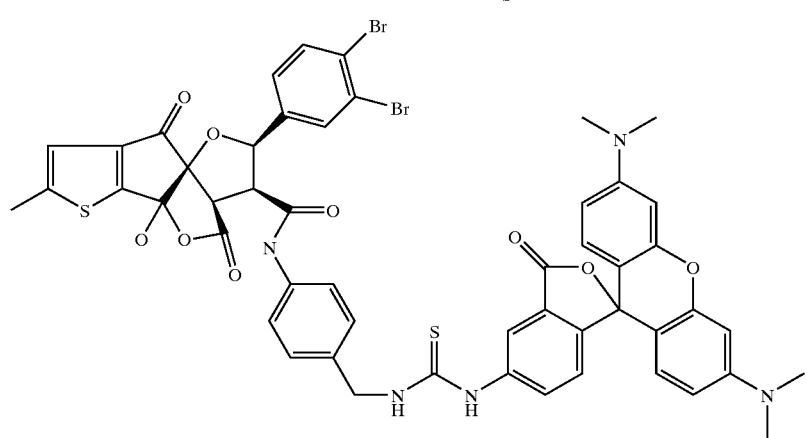
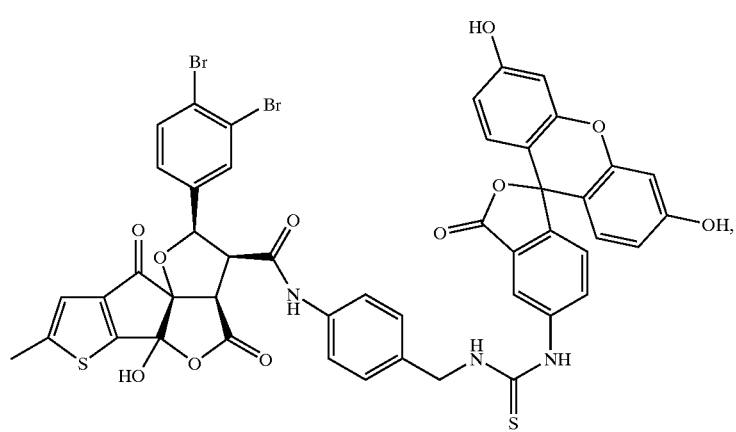
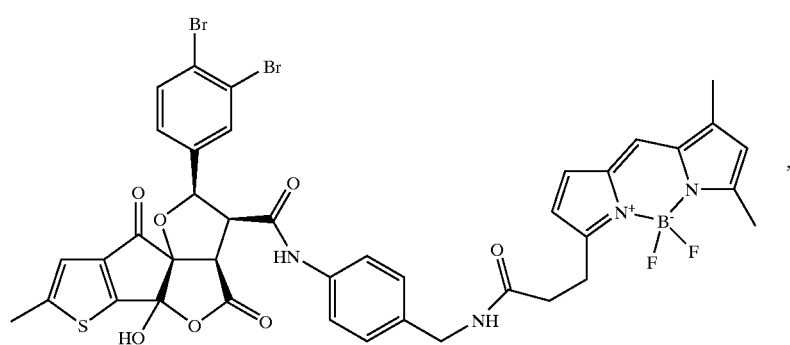

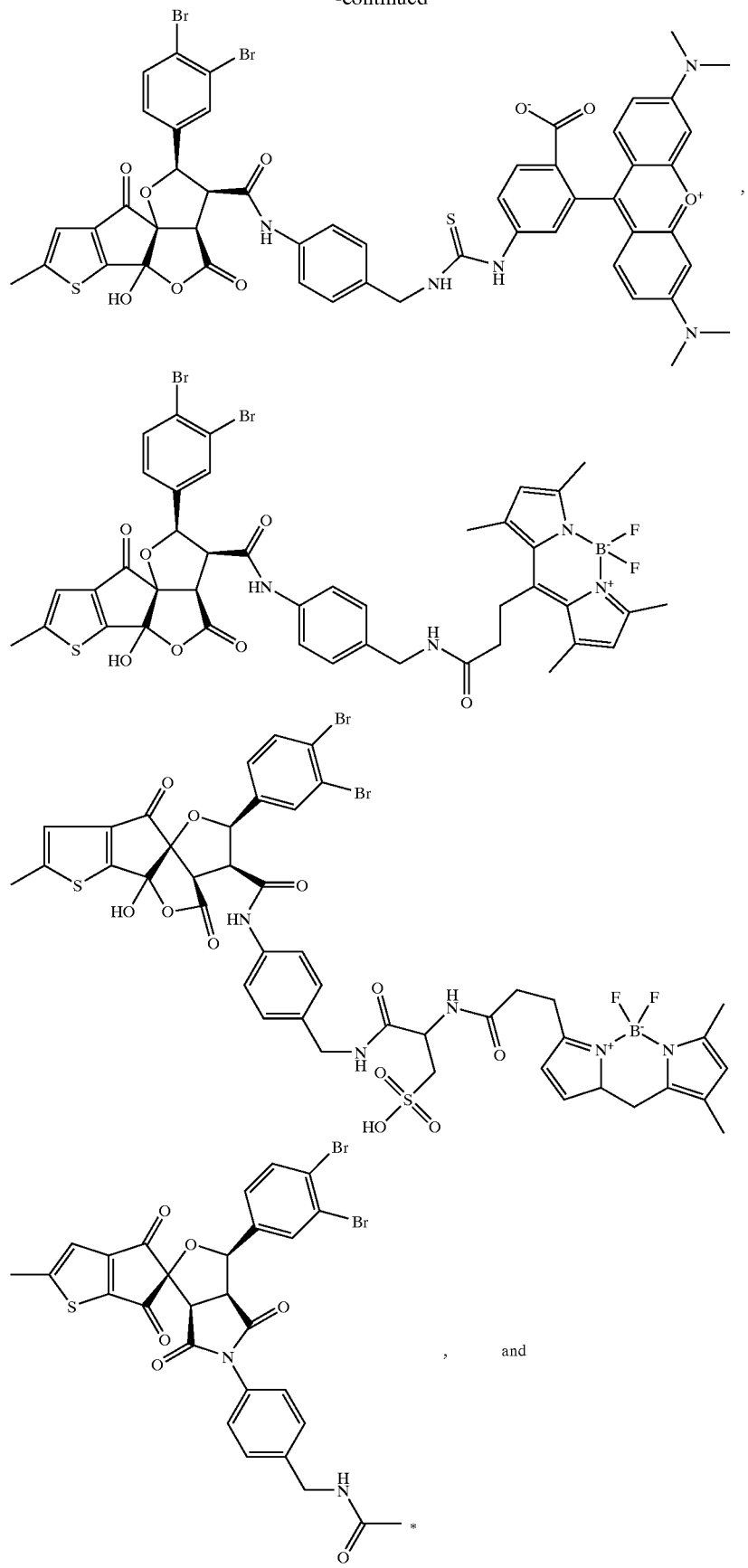

-continued

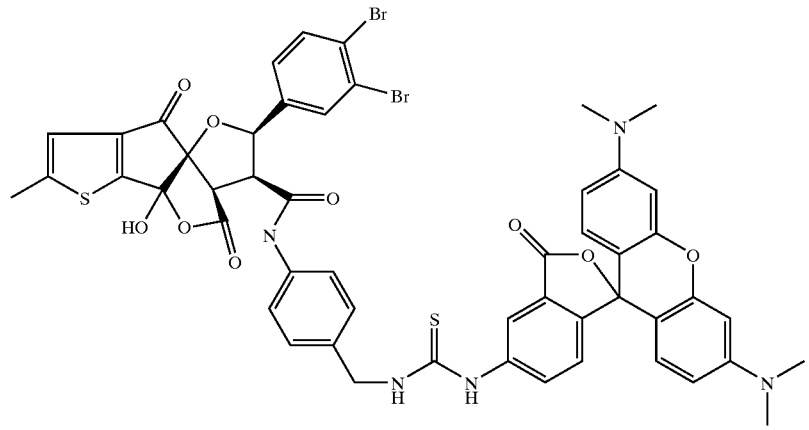

27. An assay of claim 1 for identifying inhibitors of HPV using a probe having the formula:

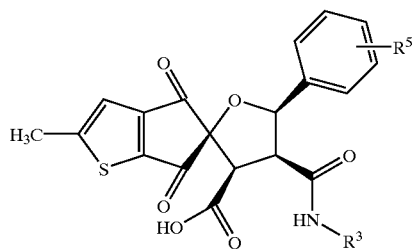

wherein $R^5$ is lower alkyl, lower cycloalkyl, lower alkoxy, halo, hydroxy, nitrile or trifluoromethyl, and $R^3$ is aryl substituted with a fluorescent label, a chemiluminescent label, or a radioactive label.

28. A kit for testing compounds that potentially bind to HPV E2, said kit comprising a probe as defined in claim 21; and instructions on how to use said probe for identifying test compounds binding to said E2.

29. A kit for testing compounds that potentially bind to the transactivation domain of HPV E2, said kit comprising a E2:probe complex as defined in claim 1; and instructions on how to use said probe for identifying test compounds binding to said transactivation domain.

30. A reagent for testing compounds that potentially bind to the transactivation domain of HPV E2, said reagent comprising a E2:probe complex as defined in claim 1.

31. The assay according to claim 5 wherein said chemiluminescent label is luciferase.

* * * * *

SEQUENCE LISTING

<160> NUMBER OF SEQ ID NOS: 5

<210> SEQ ID NO 1
<211> LENGTH: 215
<212> TYPE: PRT
<213> ORGANISM: HPV

<400> SEQUENCE: 1

Met Glu Ala Ile Ala Lys Arg Leu Asp Ala Cys Gln Asp Gln Leu Leu
1               5                   10                  15

Glu Leu Tyr Glu Glu Asn Ser Ile Asp Ile His Lys His Ile Met His
            20                  25                  30

Trp Lys Cys Ile Arg Leu Glu Ser Val Leu Leu His Lys Ala Lys Gln
        35                  40                  45

Met Gly Leu Ser His Ile Gly Leu Gln Val Val Pro Pro Leu Thr Val
    50                  55                  60

Ser Glu Thr Lys Gly His Asn Ala Ile Glu Met Gln Met His Leu Glu
65                  70                  75                  80

Ser Leu Ala Lys Thr Gln Tyr Gly Val Glu Pro Trp Thr Leu Gln Asp
            85                  90                  95

Thr Ser Tyr Glu Met Trp Leu Thr Pro Pro Lys Arg Cys Phe Lys Lys
            100                 105                 110

Gln Gly Asn Thr Val Glu Val Lys Phe Asp Gly Cys Glu Asp Asn Val
        115                 120                 125

Met Glu Tyr Val Val Trp Thr His Ile Tyr Leu Gln Asp Asn Asp Ser
    130                 135                 140

Trp Val Lys Val Thr Ser Ser Val Asp Ala Lys Gly Ile Tyr Tyr Thr
145                 150                 155                 160

Cys Gly Gln Phe Lys Thr Tyr Tyr Val Asn Phe Asn Lys Glu Ala Gln
                165                 170                 175

Lys Tyr Gly Ser Thr Asn His Trp Glu Val Cys Tyr Gly Ser Thr Val
            180                 185                 190

Ile Cys Ser Pro Ala Ser Val Ser Ser Thr Val Arg Glu Val Ser Ile
        195                 200                 205

Ala Glu Pro Thr Thr Tyr Thr
    210                 215

<210> SEQ ID NO 2
<211> LENGTH: 236
<212> TYPE: PRT
<213> ORGANISM: HPV

<400> SEQUENCE: 2

Met Ala Ser Met Thr Gly Gly Gln Gln Met Gly Arg Gly Ser Glu Ala
1               5                   10                  15

Ile Ala Lys Arg Leu Asp Ala Cys Gln Asp Gln Leu Leu Glu Leu Tyr
            20                  25                  30

Glu Glu Asn Ser Ile Asp Ile His Lys His Ile Met His Trp Lys Cys
        35                  40                  45

Ile Arg Leu Glu Ser Val Leu Leu His Lys Ala Lys Gln Met Gly Leu

```
                    50                  55                  60
Ser His Ile Gly Leu Gln Val Val Pro Pro Leu Thr Val Ser Glu Thr
 65                  70                  75                  80

Lys Gly His Asn Ala Ile Glu Met Gln Met His Leu Glu Ser Leu Ala
                 85                  90                  95

Lys Thr Gln Tyr Gly Val Glu Pro Trp Thr Leu Gln Asp Thr Ser Tyr
                100                 105                 110

Glu Met Trp Leu Thr Pro Pro Lys Arg Cys Phe Lys Lys Gln Gly Asn
            115                 120                 125

Thr Val Glu Val Lys Phe Asp Gly Cys Glu Asp Asn Val Met Glu Tyr
        130                 135                 140

Val Val Trp Thr His Ile Tyr Leu Gln Asp Asn Asp Ser Trp Val Lys
145                 150                 155                 160

Val Thr Ser Ser Val Asp Ala Lys Gly Ile Tyr Tyr Thr Cys Gly Gln
                165                 170                 175

Phe Lys Thr Tyr Tyr Val Asn Phe Asn Lys Glu Ala Gln Lys Tyr Gly
            180                 185                 190

Ser Thr Asn His Trp Glu Val Cys Tyr Gly Ser Thr Val Ile Cys Ser
        195                 200                 205

Pro Ala Ser Val Ser Ser Thr Val Arg Glu Val Ser Ile Ala Glu Pro
    210                 215                 220

Thr Thr Tyr Thr Leu Glu His His His His His His
225                 230                 235

<210> SEQ ID NO 3
<211> LENGTH: 37
<212> TYPE: DNA
<213> ORGANISM: Artificial Sequence
<220> FEATURE:
<223> OTHER INFORMATION: Primer

<400> SEQUENCE: 3
gcggcgggat ccgaagcaat agccaagcgt ttagatg                          37

<210> SEQ ID NO 4
<211> LENGTH: 37
<212> TYPE: DNA
<213> ORGANISM: Artificial Sequence
<220> FEATURE:
<223> OTHER INFORMATION: Primer

<400> SEQUENCE: 4
gcggcgctcg agggtgtatg tagtaggttc agcaatg                          37

<210> SEQ ID NO 5
<211> LENGTH: 195
<212> TYPE: PRT
<213> ORGANISM: HPV

<400> SEQUENCE: 5

Met Glu Ala Ile Ala Lys Arg Leu Asp Ala Cys Gln Asp Gln Leu Leu
 1                5                  10                  15

Glu Leu Tyr Glu Glu Asn Ser Ile Asp Ile His Lys His Ile Met His
                20                  25                  30

Trp Lys Cys Ile Arg Leu Glu Ser Val Leu Leu His Lys Ala Lys Gln
            35                  40                  45

Met Gly Leu Ser His Ile Gly Leu Gln Val Val Pro Pro Leu Thr Val
        50                  55                  60
```

```
Ser Glu Thr Lys Gly His Asn Ala Ile Glu Met Gln Met His Leu Glu
65                  70              75                  80

Ser Leu Ala Lys Thr Gln Tyr Gly Val Glu Pro Trp Thr Leu Gln Asp
                85              90                  95

Thr Ser Tyr Glu Met Trp Leu Thr Pro Pro Lys Arg Cys Phe Lys Lys
            100             105                 110

Gln Gly Asn Thr Val Glu Val Lys Phe Asp Gly Cys Glu Asp Asn Val
            115             120                 125

Met Glu Tyr Val Val Trp Thr His Ile Tyr Leu Gln Asp Asn Asp Ser
    130             135             140

Trp Val Lys Val Thr Ser Ser Val Asp Ala Lys Gly Ile Tyr Tyr Thr
145             150             155                     160

Cys Gly Gln Phe Lys Thr Tyr Tyr Val Asn Phe Asn Lys Glu Ala Gln
                165             170              175

Lys Tyr Gly Ser Thr Asn His Trp Glu Val Cys Tyr Gly Ser Thr Val
            180             185                 190

Ile Cys Ser
        195
```